(12) United States Patent
Paw et al.

(10) Patent No.: US 6,338,873 B1
(45) Date of Patent: Jan. 15, 2002

(54) METHOD OF FORMING GROUP II METAL-CONTAINING FILMS UTILIZING GROUP II MOCVD SOURCE REAGENTS

(75) Inventors: Witold Paw, Danbury; Thomas H. Baum, New Fairfield, both of CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/610,822

(22) Filed: Jul. 6, 2000

Related U.S. Application Data

(62) Division of application No. 09/067,557, filed on Apr. 28, 1998, now Pat. No. 6,111,122.

(51) Int. Cl.⁷ .......................... C23C 16/00; C23C 16/06
(52) U.S. Cl. .................................. 427/252; 427/255.32
(58) Field of Search .............................. 427/252, 255.32

(56) References Cited

U.S. PATENT DOCUMENTS

| | | | |
|---|---|---|---|
| 5,204,314 A | | 4/1993 | Kirlin et al. |
| 5,248,787 A | * | 9/1993 | Timmer et al. ............. 549/206 |
| 5,280,012 A | | 1/1994 | Kirlin et al. |
| 5,453,494 A | | 9/1995 | Kirlin et al. |
| 5,478,610 A | | 12/1995 | Desu et al. |
| 5,504,195 A | | 4/1996 | Leedham et al. |
| 5,536,323 A | | 7/1996 | Kirlin et al. |
| 5,648,114 A | | 7/1997 | Paz De Araujo et al. |
| 5,696,240 A | | 12/1997 | Vallarino et al. ............. 534/15 |
| 5,948,322 A | * | 9/1999 | Baum et al. ................. 252/584 |
| 6,025,222 A | * | 2/2000 | Kimura et al. ............... 438/240 |

OTHER PUBLICATIONS

Zang, et al., "Organometallic Chemical Vapor Deposition of High Tc Superconducting Bi–Sr–Ca–Cu–O Films," Appl. Phys. Lett., 54(12) Mar. 20, 1989, pp. 1166–1168.

Bhandari, et al., "Comparison of (L)M(thd)2(M=Mg, Ca, Sr, Ba; L–Tetraglyme, PMDETA) Precursors for high K Dielectric MOCVD", MRS Symposium Proceedings, Fall 1996, Materials Research Society Meeting, pp. 1–6.

Van Buskirk, et al., Manufacturing of Perovskite Thin Films Using Liquid Delivery MOCVD, Integrated Ferroelectrics, 1995, vol. 10, pp. 9–22.

Beach, et al., ""MOCVD of Very Thin Films of Lead Lanthanum Titanate, Mater. Res. Soc. Symp. Proc., vol. 415, (1996), pp. 225–230.

Fukin, et al. "Crystal and Molecular Structure of Bismuth Dipiroloylmethonate," Russian Journal of Inorganic Chemicals, vol. 38, No. 7 (1993), pp. 1119–1123.

Kimura, et al., Jpn. J. Appl. Phys. Sep. 1994, 33, 5119–5124.

Fenton, et al., J. Chem. Soc. A 1971, 22, 3481–3485.

Drew, et al., J. Chem. Soc. Dalton Trans. 1981, 8, 1678–1684.

Bhandari. et al., Mat. Res. Soc. Symp. Proc. 1997, 446, 327–332.

Gardiner, et al. Chem. Mater. 1994, 6(11), 1967–1970.

Kimura, T. et al. Synthesis of Novel Sr Source for Metalorganic Chemical Vapor Deposition of SrTiO3 Japanese Journal of Applied Physics, Sep. 1994, vol. 33, No. 9B, pp. 5119–5124; see the abstract, Figure 1 structures 44 and 45, and Figure 4.

Gardomer. R.A., et al. Mononuclear Barium Diketonate Polyamine Adducts. Synthesis, Structures, and use in MOCVD of Barium Titanate. Chemistry of Materials, 1994, vol. 6, pp. 1967–1970; see the abstract.

Webster'Ninth New Collegiate Dictionary, Merriam–Webster Inc., Springfield, Massachusetts, 1990, p. 247.

Drew, M.G.B. et al. Metal–ion–controlled Transamination in the Synthesis of Macrocylic Schiff–Bassse Ligands. Part 2. Stepwise Synthesis, Ring Expansion/Contraction, and the Crystal and Molecular Structure of a Ten–coordinate Barium (II) Complex. Journal of the Chemical Society Dalton transaction, 1981, vol. 8, pp. 1768–1784; see the first paragraph in the Results and Discussion section on p. 1678, and the first paragraph in the Ring–closure Reactions section of p. 1680.

* cited by examiner

Primary Examiner—Brian K. Talbot
(74) Attorney, Agent, or Firm—Marianne Fuierer; Margaret Chappuis; Robert A. McLauchlan

(57) ABSTRACT

Novel Group II metal MOCVD precursor compositions are described having utility for MOCVD of the corresponding Group II metal-containing films. The complexes are Group II metal β-diketonate Lewis base adducts having ligands such as: (i) amines bearing terminal $NH_2$ groups; (ii) imine ligands formed as amine (i)/carbonyl reaction products; (iii) combination of two or more of the foregoing ligands (i)–(ii), and (iv) combination of one or more of the foregoing ligands (i)–(ii) with one or more other ligands or solvents. The source reagent complexes of barium and strontium are usefully employed in the formation of barium strontium titanate and other Group II doped thin-films on substrates for microelectronic device applications, such as integrated circuits, ferroelectric memories, switches, radiation detectors, thin-film capacitors, microelectromechanical structures (MEMS) and holographic storage media.

9 Claims, 12 Drawing Sheets

METHOD OF FORMING GROUP II METAL-CONTAINING FILMS UTILIZING GROUP II MOCVD SOURCE REAGENTS

This is a division of U.S. application Ser. No. 09/067,557 filed Apr. 28, 1998, now U.S. Pat. No. 6,111,127.

BACKGROUND OF THE INVENTION

1. Field Of The Invention

The present invention relates to Group II precursor compositions and their synthesis, and to a method of forming a Group II metal-containing films on a substrate by metalorganic chemical vapor deposition (MOCVD) utilizing such precursor compositions.

2. Description of the Related Art

Many materials are utilized in the form of thin films on substrates and are formed by vapor deposition techniques.

A number of Group II metal (Ba, Sr, Ca, Mg)-containing films fall in this category. These encompass refractory thin film high temperature superconducting (HTSC) compositions including $YBa_2Cu_3O_x$, wherein x is from about 6 to 7.3, BiSrCaCuO, and TlBaCaCuO. Other Group II metal-containing films include barium titanate, $BaTiO_3$, and barium strontium titanate, $Ba_xSr_{1-x}TiO_3$ (BST), which have been identified as ferroelectric, photonic and electronic materials with unique and potentially very useful properties in thin film applications of such materials. Still other Group II metal-containing films include materials such as $Ba_xSr_{1-x}Nb_2O_6$, which is a photonic material whose index of refraction changes as a function of electric field and also as a function of the intensity of irradiated light. Additional Group II metal-containing films include Group II metal fluorides such as $BaF_2$, $CaF_2$, and $SrF_2$, which are useful for scintillation detecting and coating of optical fibers, and Group II doped lanthanum manganites, such as $La_{1-x}Ca_xMnO_3$.

Many of the potential applications of these materials require their use in thin film (<1000 $\mu$m) coatings, or layer form. The films or layers may also be advantageously epitaxially related to the substrate upon which they are formed. Applications in which materials may need to be deposited in film or layer form include integrated circuits, switches, radiation detectors, thin film capacitors, holographic storage media, and various other microelectronic devices.

Chemical vapor deposition (CVD) is a particularly attractive method for forming these layers because it is readily scaled up for production. Further, the electronic industry has extensive experience and an established CVD equipment base that can be applied to new CVD processes. In general, the control of key variables such as film stoichiometry and thickness, and the coating of a wide variety of substrate geometries is possible with CVD. Forming the thin films by CVD permits the integration of these materials into existing device production technologies. CVD also permits the formation of layers of materials that are epitaxially grown on substrates having close crystal structures and lattice parameters.

CVD requires that the element source reagents, i.e., the precursor compounds and complexes containing the elements or components of interest, must be sufficiently volatile to permit gas phase transport into the chemical vapor deposition reactor. The elemental precursor must decompose in the CVD reactor to deposit only the desired element at the desired growth temperatures. Premature gas phase reactions leading to particulate formation must not occur, nor should the source reagent decompose in the lines before reaching the reactor deposition chamber. When compounds are decomposed for deposition, obtaining optimal properties requires close control of stoichiometry that can only be achieved if the reagent can be delivered into the reactor in a controllable fashion. In this respect the reagents must not be so chemically stable that they are non-reactive in the deposition chamber.

Desirable CVD reagents, therefore, are fairly reactive and volatile. Unfortunately, for many of the materials described above, volatile reagents do not exist. Many potentially highly useful refractory materials have in common that one or more of their components are Group II elements, e.g., the metals barium, calcium, strontium, or magnesium, for which no or few volatile compounds well-suited for CVD are known. In many cases, the source reagents are solids whose sublimation temperature is very close to the decomposition temperature. Therefore, the reagent may begin to decompose in the lines during transport to the reactor, and it therefore is very difficult to control the stoichiometry of the deposited films from such decomposition—susceptible reagents.

When the film being deposited by CVD is a multicomponent substance, such as barium titanate or the oxide superconductors, rather than a pure element, controlling the film stoichiometry is critical to obtaining the desired film properties (optical and/or electrical properties). In the deposition of such materials, which may form films with a wide range of stoichiometries, the controlled delivery of known proportions of the source reagents into the CVD reactor chamber is essential.

In other cases, the CVD source reagents are liquids, or are dissolvable or suspendable in solvents to form liquid precursor compositions. Such liquid precursors are suitable for liquid delivery CVD. Liquid delivery CVD as a process has a number of desirable features in relation to other reagent delivery techniques, such as conventional bubbler delivery, liquids. Nonetheless, the delivery of liquid precursors into the CVD reactor (in the vapor phase) after their vaporization has proven difficult in many instances because of problems of premature decomposition and/or stoichiometry control.

Thus, while precursor liquid delivery systems present distinct advantages over conventional techniques, there is often some fraction of the precursor compound that decomposes into very low volatility compounds that remain in the vaporization zone. This deficiency is an important issue in the operation of CVD processes that use thermally unstable solid source precursors that undergo significant decomposition at conditions needed for sublimation. Such decomposition can occur in all reagent delivery systems that involve a vaporization step, including flash vaporizer liquid delivery systems, as well as more conventional reagent delivery systems that include bubblers and heated vessels operated without carrier gas.

Optimization of the conditions used in the vaporizer of precursor delivery systems can minimize the precursor decomposition in the vaporization zone, but virtually all solid precursors decompose to some extent near their vaporization temperature. Although the use of these precursors may be mandated by availability or economics, thermal decomposition should be minimized during gas-phase transport. Use of liquid precursors, however, can alleviate some of the decomposition and residue problems encountered with solid source delivery systems. The elimination of solid precursors can also reduce the formation of particles and improve the vaporizer mean-time to maintenance.

Despite the advantages of the liquid delivery approach (which include improved precision and accuracy for most liquid and solid CVD precursors and higher delivery rates), the foregoing deficiencies pose a serious impediment to widespread use of the liquid delivery technique for providing volatilized reagent to the CVD reactor in the full-scale manufacturing of electronic components.

The foregoing problems have specifically been experienced in the development of high-density memories using high dielectric constant and ferroelectric materials. In addition to high-density memories, ferroelectric materials are attractive candidates in a wide variety of solid state sensors and imaging devices, as a consequence of their pyroelectric and piezoelectric properties. Production worthy deposition modules are needed to realize the full potential of ferroelectric materials in evolving semiconductors. The preferred method for production of films of these ferroelectric materials is MOCVD, but at present a full compliment of stable liquid precursors is not commercially available for many ferroelectric thins films of interest, such as $BaSrTiO_3$ and $BiSr_2Ta_2O_9$.

The vaporization of solid Group II precursors such as those used in the MOCVD of these materials typically undergo some decomposition during vaporization. Oligomerization or polymerization may accompany decomposition and reduce the effective transport rate of the precursors more rapidly than expected based upon the amount of decomposed material. This phenomenon can lead to inefficient transport, particle formation, decomposition residue, loss of film stoichiometry and process drift or irreproducibility. It is one of the reasons why many groups have designed their CVD tools to allow the bubblers to be loaded with a fresh charge of precursor prior to each run. See, for example, J. M. Zhang, J. Zhao, H. O. Marcy, L. M. Tonge, B. M. Wessels, T. J. Marks, and C. R. Kannewurf, *Appl. Phys. Lett.*, 54, 1166 (1989).

Further, the Group II precursor materials do not have high vapor pressures, so all sections of the reactor between the vaporization point and any trap used to remove undecomposed precursor before the vacuum pump must be heated. This brings considerable added complexity and expense to the reactor design. In particular, cost and complexity rise steeply with increase of required temperatures from around 180° C. to 240° C. This is because elastomer vacuum seals cannot withstand temperatures above the 200–220° C. range and therefore, metal seals must be used. The development of liquid precursors that can be vaporized and will not condense as solids on the reactor walls at lower temperatures would entail significant commercial advantages for the production of Group II element-containing films, such as BST.

Improved liquid delivery systems are disclosed in U.S. Pat. No. 5,204,314 issued Apr. 20, 1993 to Peter S. Kirlin et al. and U.S. Pat. No. 5,536,323 issued Jul. 16, 1996 to Peter S. Kirlin et al., which describe heated vaporization structures such as microporous disk elements. In use, liquid source reagent compositions are flowed onto the foraminous vaporization structure for flash vaporization. Vapor thereby is produced for transport to the deposition zone, e.g., a CVD reactor. The liquid delivery systems of these patents provide high efficiency generation of vapor from which films may be grown on substrates. Such liquid delivery systems are usefully employed for generation of multicomponent vapors from corresponding liquid reagent solutions containing one or more precursors as solutes, or alternatively from liquid reagent suspensions containing one or more precursors as soluble suspensions. Other methodologies, such as aerosol generation can be envisioned, as well.

The art continues to seek improvements in Group II metal source reagent compositions, and in liquid delivery systems for vapor-phase formation of advanced materials comprising Group II metal(s).

The invention described hereinafter involves the synthesis of novel liquid, or low melting solid, Group II metal precursors, since the existing Ba and Sr precursors are solids and generally associated with unacceptable levels of particle formation, and vaporizer or delivery tube clogging. As a result, such precursors thus do not fully satisfy the requirements of the CVD process for manufacturing semiconductor components.

Designing liquid or low melting point solid Group II CVD precursors represents a significant challenge. For example, the difficulties in obtaining suitable barium precursors stem from the highly electropositive character of barium with its large ionic radius. High coordination numbers are present in useful barium coordination complexes that have utility for CVD to produce barium-containing films. Such high coordination numbers have to be satisfied by mostly neutral ligands that coordinate weakly to the electropositive Ba center.

As a result, the Ba CVD precursors synthesized to date are predominantly characterized by insufficient thermal stability. The lability of metal-ligand bonds in Ba metalorganics coupled with the large size of the metal center result in the tendency to aggregate to form multinuclear Ba species. The formation of multinuclear species can occur during synthesis, affecting the volatility of the precursor, or during the CVD process, leading to particle formation, lowered precursor transport and film growth efficiency. Formation of multinuclear species also results in decreased solubility, which is an important parameter of the liquid delivery CVD process.

In prior art synthesis of barium precursors, it was difficult to form very stable and highly volatile complexes of barium. As a result, synthesis efforts have focused on achieving an appropriate mix of volatility and stability for a given precursor to facilitate its use in CVD applications. Similar issues and considerations are presented in the development of other Group II metal (e.g., Ca, Sr, and Mg) precursors.

In view of the foregoing, it is an object of the present invention to provide new Group II precursor compositions which are usefully employed in liquid delivery MOCVD processes to form Group II metal-containing films.

It is another object of the present invention to provide new Group II precursor compositions for forming ferroelectric films of materials such as SBT, and high dielectric constant films of materials such as BST.

It is yet another object of the present invention to provide an efficient liquid delivery process for forming Group II metal-containing films such as BST films.

Other objects and advantages of the present invention will be more fully apparent from the ensuing disclosure and appended claims.

SUMMARY OF THE INVENTION

The present invention relates to Group II metal source reagents useful in liquid delivery MOCVD for the deposition of Group II metal-containing films.

In one aspect, the invention relates to a Group II metal β-diketonate adduct composition selected from the group consisting of alkyl, fluoroalkyl and perfluoroalkyl substituted β-diketonate ligands.

More specifically, the invention relates in one compositional aspect to a Group II metal β-diketonate adduct com position including ligands selected from the group consisting of:
  (i) amines, e.g., an aliphatic amine, ether amine, etc., bearing terminal $NH_2$ groups;
  (ii) imines produced as the reaction product of an amine ligand moiety (as specified in (i)) and a carbonyl compound (e.g., a compound containing at least one carbonyl group, such as a ketone, aldehyde, diketone or dialdehyde compound);
  (iii) combination of two or more of the foregoing ligands (i)–(ii),
  (iv) combination of at least one of the foregoing ligands (i)–(ii) with one or more other ligands, such as THF.

A further aspect of the invention relates to a Group II metal β-diketonate adduct composition including at least one adduct ligand selected from the group consisting of ligands of the formulae:
  (i) $H_2N$—G—$NH_2$, wherein G is a divalent moiety selected from the group consisting of (—$CH_2$—)$_x$, (—CH—)$_x$, amine groups, ether groups, and combinations thereof, wherein x is from 1 to 10 inclusive;
  (ii) $R_1R_2C$=N—G—N=$CR_1R_2$ wherein $R_1$ and $R_2$ are independently alkyl, fluoroalkyl or $R_1$ and $R_2$ together with the adjacent carbon atom form a cycloalkyl group, and wherein G is as described above; and
  (iii) $R_1R_2C$=N—G—$NH_2$ wherein $R_1$ and $R_2$ are independently alkyl, fluoroalkyl or $R_1$ and $R_2$ together with the adjacent carbon atom form a cycloalkyl group, and wherein G is as described above,
provided that when two or more adduct ligands are present in the composition, each is independently selected from said group of ligands (i)–(iii).

In one specific compositional aspect, the invention relates to a barium bis (2,2,6,6-tetramethyl-3,5-heptanedionate) complex having a clear viscous oil form, and including polyimine ligands selected from the group consisting of ligands (A) and (B):

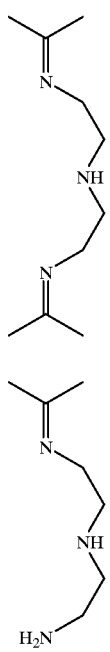

Another compositional aspect relates to a strontium bis (2,2,6,6-tetramethyl-3,5-heptanedionate) imine adduct having a generally clear viscous oil form and including polyimine ligands selected from the group consisting of ligands (A) and (B):

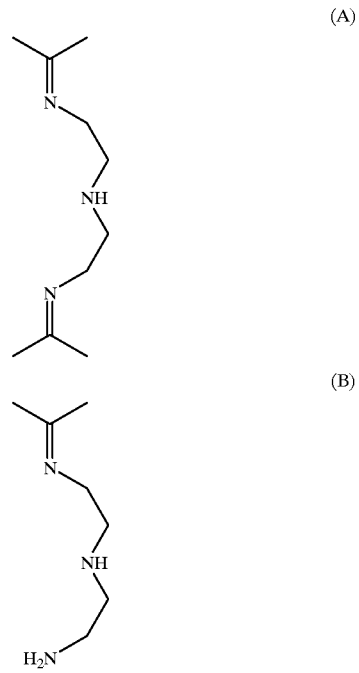

A further aspect of the invention relates to a method of making a Group II metal β-diketonate adduct source reagent including a coordinated ligand L, comprising the steps of a synthesis selected from the following synthesis schemes (1)–(4):

Scheme (1)
  providing a Group II metal β-diketonate complex including a ligand L coordinated to the Group II metal atom, wherein L is an amine with terminal —$NH_2$ groups;
  reacting the Group II metal β-diketonate complex with an excess of carbonyl group-containing reagent in the presence or absence of a desiccant to form as a reaction product
  a Group II metal β-diketonate complex including at least one imine (—N=C<) group-containing ligand, and unreacted carbonyl group-containing reagent;
  separating the desiccant if present;
  removing the unreacted carbonyl group-containing reagent from the reaction product, to recover the Group II metal β-diketonate complex including at least one imine (—N=C<) group-containing ligand, as said Group II metal β-diketonate adduct source reagent;

Scheme (2)
  providing a Group II metal β-diketonate complex including a ligand L coordinated to the Group II metal atom, wherein L is an amine with terminal —$NH_2$ groups;
  reacting the Group II metal β-diketonate complex with a stoichiometric amount of carbonyl group-containing reagent in an organic solvent in the presence or absence of a desiccant to form as a reaction product a Group II metal β-diketonate complex including at least one imine (—N=C<)group-containing ligand dissolved in that solvent;

separating the desiccant if present;
removing the solvent to recover the Group II metal β-diketonate complex including at least one imine (—N═C<) group-containing ligand, as said Group II metal β-diketonate adduct source reagent;

Scheme (3)
reacting an amine with terminal —NH$_2$ groups with an excess of carbonyl group-containing reagent in the presence or absence of a desiccant to form a reaction product including at least one imine (—N═C<) group, and unreacted carbonyl group-containing reagent;
separating the desiccant if present;
removing the unreacted carbonyl group-containing, reagent from the reaction product, to recover an imine including at least one imine (—N═C<) group,
reacting the stoichiometric amount of the imine product with a Group II metal β-diketonate complex of general formula [M(β-diketonate)$_2$]$_n$, wherein n is a number from 1 to 4 inclusive, in an organic solvent to form a reaction product including a Group II metal β-diketonate complex including at least one imine (—N═C<) group-containing ligand dissolved in that solvent;
removing the solvent from the reaction product, to recover the Group II metal β-diketonate complex including at least one imine (—N═C<) group-containing ligand, as said Group II metal β-diketonate adduct source reagent.

Scheme (4)
reacting an amine with terminal —NH$_2$ groups with a stoichiometric amount of carbonyl group-containing reagent in an organic solvent in the presence or absence of a desiccant to form a reaction product including at least one imine (—N═C<) group, and unreacted carbonyl group-containing reagent;
separating the desiccant if present;
removing the solvent, to recover an imine including at least one imine (—N═C<) group,
reacting the stoichiometric amount of the imine product with a Group II metal β-diketonate complex of general formula [M(β-diketonate)$_2$]$_n$, wherein n is a number from 1 to 4 inclusive, in an organic solvent to form a reaction product including a Group II metal β-diketonate complex including at least one imine (—N═C<) group-containing ligand dissolved in that solvent;
removing the solvent from the reaction product, to recover the Group II metal β-diketonate complex including at least one imine (—N═C<) group-containing ligand, as said Group II metal β-diketonate adduct source reagent.

In a further aspect, the invention relates to a method of forming a Group II metal-containing film on a substrate, comprising the steps of:
providing a liquid delivery apparatus including a vaporizer and a chemical vapor deposition zone;
transporting a liquid precursor composition for said Group II metal-containing film to the vaporizer of the liquid delivery apparatus for vaporization of the precursor composition to yield a vapor-phase Group II metal precursor composition; and
flowing the vapor-phase metal precursor composition to the chemical vapor deposition zone for deposition of Group II metal on the substrate from the vapor-phase Group II metal precursor composition to form the Group II metal-containing film,
in which the liquid precursor material includes a Group II metal β-diketonate complex incorporating therein ligands selected from the group consisting of:
(i) amines, e.g., an aliphatic amine, ether amine, etc., bearing terminal NH$_2$ groups;
(ii) imines produced as the reaction product of an amine ligand moiety (as specified in (i)) and a carbonyl compound (e.g., a compound containing at least one carbonyl group, such as a ketone, aldehyde, diketone or dialdehyde compound);
(iii) combination of two or more of the foregoing ligands (i)–(ii),
(iv) combination of at least one of the foregoing ligands (i)–(ii) with one or more other ligands, such as THF.

A further aspect of the invention relates to a liquid delivery process for forming a BST film on a substrate, comprising the steps of:
providing liquid precursors for each of the barium, strontium and titanium components of the BST film;
vaporizing each of the liquid precursors to form corresponding precursor vapor; and
contacting the precursor vapor with a substrate to deposit barium, strontium and titanium thereon;
wherein said liquid precursors for barium and strontium comprise respective barium and strontium precursor complexes, and at least one of the barium and strontium precursors comprises a corresponding metal β-diketonate adduct complex including ligands selected from the group consisting of:
(i) amines, e.g., an aliphatic amine, ether amine, etc., bearing terminal NH$_2$ groups;
(ii) imines produced as the reaction product of an amine ligand moiety (as specified in (i)) and a carbonyl compound (e.g., a compound containing at least one carbonyl group, such as a ketone, aldehyde, diketone or dialdehyde compound);
(iii) combination of two or more of the foregoing ligands (i)–(ii),
(iv) combination of at least one of the foregoing ligands (i)–(ii) with one or more other ligands, such as THF.

Other aspects and features of the invention will be more fully apparent from the ensuing disclosure and appended claims.

DETAILED DESCRIPTION OF THE INVENTION, AND PREFERRED EMBODIMENTS THEREOF

Figure 1A:
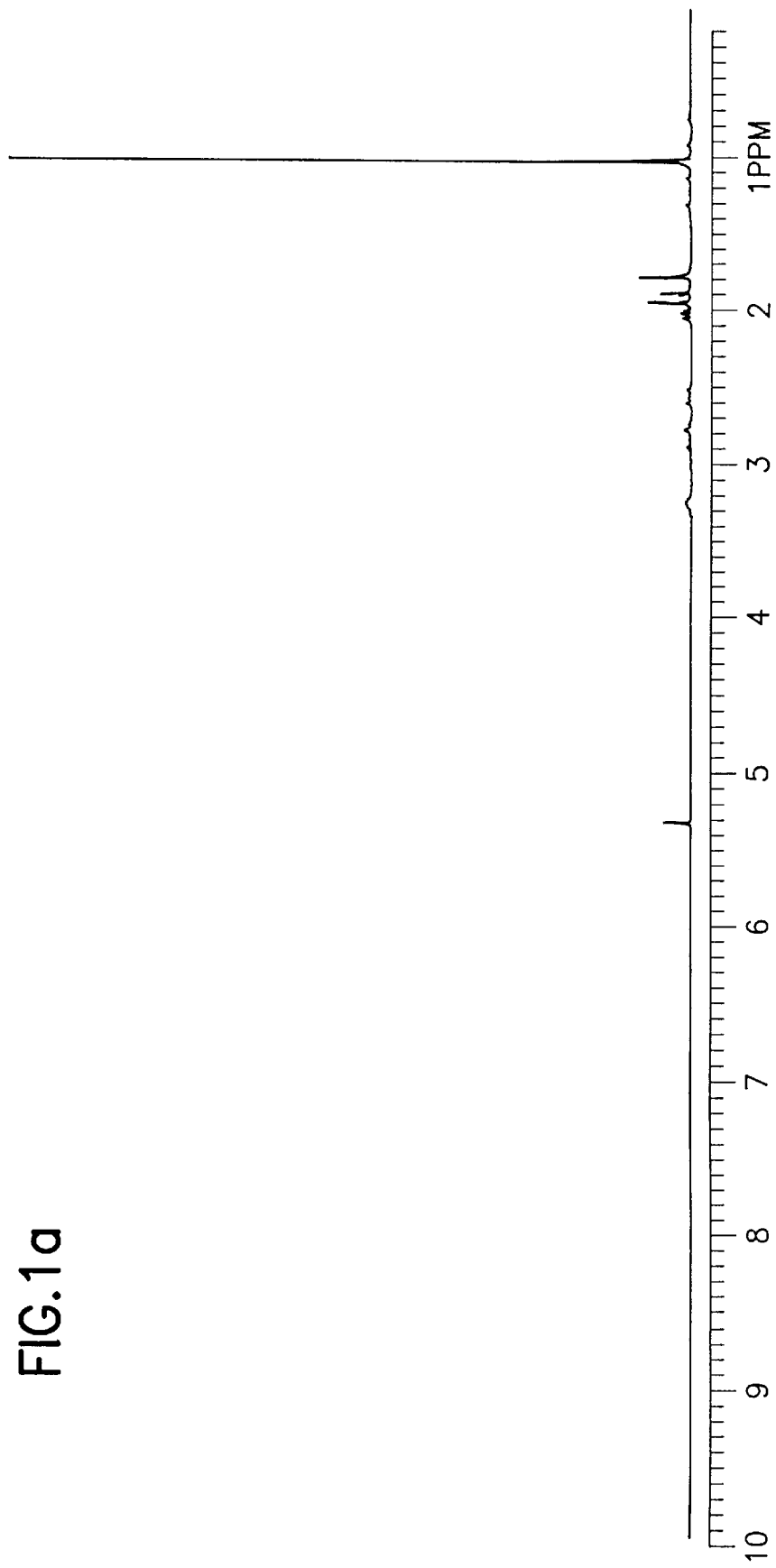
FIG. 1 (including parts (a) and (b) thereof) is the $^1$H NMR spectrum of the product of reaction of Ba(thd)$_2$(deta)$_2$ with acetone.

The disclosures of the following United States patents and patent applications are hereby incorporated herein by reference in their entirety:

U.S. patent application Ser. No. 08/835,768 filed Apr. 8, 1997 in the names of Thomas H. Baum, et al.;

U.S. patent application Ser. No. 08/484,654 filed Jun. 7, 1995 in the names of Robin A. Gardiner et al.;

U.S. patent application Ser. No. 08/414,504 filed Mar. 31, 1995 in the names of Robin A. Gardiner et al.;

U.S. application Ser. No. 08/280,143 filed Jul. 25, 1994, in the names of Peter S. Kirlin, et al.;

U.S. patent application Ser. No. 07/927,134, filed Aug. 7, 1992 in the same names;

U.S. patent application Ser. No. 07/807,807, filed Dec. 13, 1991 in the names of Peter S. Kirlin, et al., now issued as U.S. Pat. No. 5,204,314;

U.S. application Ser. No. 08/181,800 filed Jan. 15, 1994 in the names of Peter S. Kirlin, et al., and issued as U.S. Pat. No. 5,453,494;

U.S. application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990;

U.S. application Ser. No. 07/581,631 filed Sep. 12, 1990 in the names of Peter S. Kirlin, et al., and issued Jul. 6, 1993 as U.S. Pat. No. 5,225,561; and U.S. patent application Ser. No. 07/549,389 filed Jul. 6, 1990 in the names of Peter S. Kirlin, et al.

For ease of reference in the ensuing description, the following abbreviations are sometimes hereinafter used for the correspondingly identified chemical species:

M=Ba (barium), Sr (strontium), Ca (calcium) or Mg (magnesium);

thd=2,2,6,6-tetramethyl-3,5-heptanedionate;

tert-Bu-iso-Pr β-diketonate=2,2,6-trimethyl-3,5-heptanedione;

hfac=hexafluoroacctylacetonate;

tod=2,2,7-trimethyl-3,5-octanedionate;

thf=tetrahydrofuran;

thp=tetrahydropyran;

deta=diethylenetriamine;

teta=triethylenetetraamine tepa=tetraethylenepentaamine;

peteda=pentaethylentrietherdiamine deta=diethylenetriamine;

TGA=thermal gravimetric analysis;

NMR=nuclear magnetic resonance; and

STA=simultaneous thermal analysis.

The present invention provides novel Group II metal source reagent MOCVD complexes. Such complexes comprise Group II metal β-diketonate complexes incorporating adduct ligands selected from the group consisting of:

(i) amines, e.g., an aliphatic amine, ether amine, etc., bearing terminal NH$_2$ groups;

(ii) imines produced as the reaction product of an amine ligand moiety (as specified in (i)) and a carbonyl compound (e.g., a compound containing at least one carbonyl group, such as a ketone, aldehyde, diketone or dialdehyde compound);

(iii) combination of two or more of the foregoing ligands (i)–(ii), (iv) combination of at least one of the foregoing ligands (i)–(ii) with one or more other ligands, such as THF.

The role of Lewis base ligands (L) in Group II metal (β-diketonate)$_2$L complexes is to maintain coordination of the metal center and provide a mononuclear species, thereby stabilizing a low melting or liquid mononuclear conformation of the complexes. The identity and use of Lewis base ligands thereby increases both the solubility and the volatility of the complexes.

These ligands, however, typically do not bind strongly and may dissociate upon slow thermal heating. In order to negate this problem, ligands with multiple donor atoms have been used in the prior art, and in some instances β-diketonate ligands have been utilized featuring lariat polyether arms. Neither of these approaches, however, has provided significant gains in terms of thermal stability.

The present invention overcomes such difficulties in the provision of Group II metal β-diketonate adducts using ligand species that provide good coordination, good thermal stability characteristics as well as good solubility and volatility characteristics for use as MOCVD complexes.

In accordance with the invention, superior stabilities may be achieved by the use of ligands that are either synthesized around a Group II metal center (template synthesis) or synthesized prior to the formation of the complex.

The ligands used in the Group II metal β-diketonate adducts of the present invention may advantageously include any suitable species that achieve the thermal stability, volatility and solubility characteristics desired for the liquid delivery film growth process in which the Group II metal is deposited on a substrate from the Group II metal β-diketonate adduct. For example, a class of preferred adduct ligands usefully employed in the practice of the invention include imine (containing at least one imine moiety and possibly other functional groups) ligands that are formed as the reaction product of a polyamine ligand moiety and a carbonyl compound. The carbonyl compound may be any organic compound containing carbonyl group(s) and possibly other functional groups. The simplest examples of carbonyl compounds are ketones, diketones, aldehydes and dialdehydes.

Depending on the coordination structure of the source reagent complex, the complex may utilize more than one adduct ligand. For example, the source reagent complex may include two or more of the ligands described hereinabove. Alternatively, the source reagent complex may include one or more of the aforementioned ligands, together with other ligand or solvent species, e.g., tetrahydrofuran and tetrahydropyran ligands.

By way of specific examples, the Group II metal β-diketonate adduct composition may include at least one of the ligands of the general formulae:

(i) H$_2$N—G—NH$_2$, wherein G is a divalent moiety selected from the group consisting of (—CH$_2$13 )$_x$, (—CH—)$_x$, amine groups, ether groups, and combinations thereof, wherein x is from 1 to 10 inclusive, and more preferably from 1 to 6 inclusive;

(ii) $R_1R_2C=N-G-N=CR_1R_2$ wherein $R_1$ and $R_2$ are independently alkyl, fluoroalkyl or $R_1$ and $R_2$ together with the adjacent carbon atom form a cycloalkyl group, and wherein G is as described above; and (iii) $R_1R_2C=N-G-NH_2$ wherein $R_1$ and $R_2$ are independently alkyl, fluoroalkyl or $R_1$ and $R_2$ together with the adjacent carbon atom form a cycloalkyl group, and wherein G is as described above.

Examples of the formula (i) ligands include:
ethylenediamine
diethylenetriamine
1,5,8,12-tetraazadodecane
4,7,10-trioxa-1,13-tridecanediamine;
Examples of the formula (ii) and (iii) ligands include:

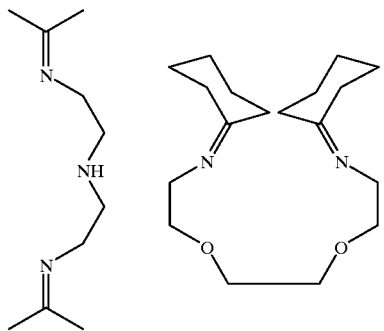

provided that when two or more adduct ligands are present in the coordinated complex, each is independently selected from the aforementioned species, whereby different ligands in the complex may be the same as or different from one another.

Considering the circumstance in which the Group II metal β-diketonate adduct composition includes at least one condensation reaction product as the adduct ligand coordinated to the Group II metal atom, such condensation reaction product may be formed by reaction of:

(1) a polyamine $H_2N-G-NH_2$, wherein G is as defined hereinabove, and (2) a carbonyl compound, viz., an organic compound containing at least one carbonyl group, optionally together with other functional groups.

The polyamine may be a species such as one or more of the following:
ethylenediamine,
diethyienetriamine,
1,5,8,12-tetraazadodecane, and
4,7,10-trioxa-1,13-tridecanediamine.

Alternatively, any other suitable polyamine species may be employed.

The co-reactant in the condensation reaction may be a ketone such as acetone, methylethylketone, methylpropylketone, dipropylketone, cyclohexanone or any other suitable species. Likewise, when an aldehyde co-reactant is employed, the aldehyde may be any suitable species, as for example acetaldehyde, formaldehyde, etc. Other carbonyl compounds belonging to other classes of organic compounds are included here with the provision that the reaction product is of the imine type and the reaction involves exclusively the carbonyl group (>C=O) present in the reactant.

The β-diketonate moiety of the Group II metal β-diketonate adduct may be any suitable β-diketonate moiety that can be coordinated to the Group II metal atom and compatible with the adducting ligand to form a complex of the desired stability, solubility and volatility characteristics. Illustrative of β-diketonate species that may be usefully employed in the broad practice of the present invention are the following:
2,2,6,6-tctramethyl-3,5-heptanedionate;
2,2,6-trimethyl-3,5-heptanedione;
hexafluoroacetylacetonate; and
2,2,7-trimethyl-3,5-octanedionate.

The Group II metal in the complex may be barium, calcium, strontium or magnesium. Precursor compositions may be formulated in the broad practice of the invention that comprise a mixture of different Group II metal complexes, wherein the Group II metals in the respective complexes are different from one another.

An example of a "cocktail" formulation of barium and strontium complexes, for the MOCVD of a barium strontium titanate film on a substrate, where the Ba/Sr precursor formulation is utilized with a precursor material of the present invention and a suitable Ti precursor for the titanium component of the film. The titanium source material may for example comprise a $Ti(O-iPr)_2(thd)_2$ source reagent in a solution including a solvent, a Lewis base ligand, tetrahydrofuran, or other compatible solvent species.

In the formation of the BST film, the respective source reagent materials in liquid form are vaporized in a vaporizer unit to form the precursor vapor. The vapor then is transported to the chemical vapor deposition reactor, containing a heated substrate that contacts the vapor to deposit the respective barium, strontium and titanium components in the desired stoichiometric relationship to one another. The deposition may be carried out in the presence of a suitable oxidant medium, to form the oxide film, or the metal film may after deposition of the respective Ba, Sr and Ti components be subjected to oxidation treatment to form the oxide film, within the skill of the art.

With particular respect to barium precursor complexes usefully employed in the practice of the invention, a highly preferred class of barium adducts includes barium bis (2,2,6,6-tetramethyl-3,5-heptanedionate) adducts displaying low melting points, or liquid physical state, and including polyamine or imine ligands such as the following:

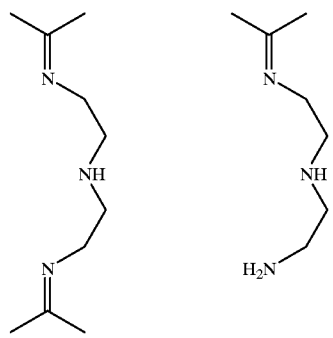

Most preferred species of the adducts of the invention include:
the barium bis (2,2,6,6-tetramethyl-3,5-heptanedionate) imine adducts displaying low melting points (e.g., <100° C.) or having the appearance of a clear or slightly yellow oil at room temperature (25° C.)

depending on the nature of the imine ligands and the method of synthesis, and the strontium bis (2,2,6,6-tetramethyl-3,5-heptanedionate) imine adduct displaying low melting points (<100° C.) or having the appearance of a clear or slightly yellow oil at room temperature, depending on the nature of the imine ligands and the method of synthesis.

The Group II metal β-diketonate adduct source reagents of the invention may be synthesized by one of the four synthesis methods described below.

In one method (Synthesis 1) of making a Group II metal β-diketonate adduct source reagent in accordance with the present invention, a Group II metal β-diketonate complex is provided that includes a ligand L coordinated to the Group II metal atom. The ligand L is an amine with terminal —NH$_2$ groups. This Group II metal β-diketonate complex is reacted with an excess of carbonyl group-containing reagent, in the presence or absence of a desiccant, to form a reaction product including the unreacted carbonyl group-containing reagent, and a Group II metal β-diketonate complex including at least one imine (—N=C<) group-containing ligand.

Upon separation of the desiccant, if present, the unreacted carbonyl group-containing reagent is removed from the reaction product, to recover the Group II metal β-diketonate complex including the imine (—N=C<) group-containing ligand, as the product source reagent.

In another method (Synthesis 2) of making a Group II metal β-diketonate adduct source reagent in accordance with the present invention, a Group II metal β-diketonate complex is provided that includes a ligand L coordinated to the Group II metal atom. The ligand L is an amine with terminal —NH$_2$ groups. This Group II metal β-diketonate complex is reacted with a stoichiometric amount of carbonyl group-containing reagent in an organic solvent in the presence or absence of a desiccant to form a reaction product, a Group II metal β-diketonate complex including at least one imine (—N=C<)group-containing ligand dissolved in a solvent.

Upon separation of the desiccant, if present, the solvent is removed from the reaction product, to recover the Group II metal β-diketonate complex including the imine (—N=C<) group-containing ligand, as the product source reagent.

In another method (Scheme 3), a polyamine with terminal —NH$_2$ groups is reacted with an excess of carbonyl group-containing reagent in the presence or absence of a desiccant to form a reaction product including a t least one imine (—N=C<) group, and unreacted carbonyl group-containing reagent.

Upon separation of the desiccant if present, the excess of the carbonyl reagent is removed from the reaction product, to yield the imine (—N=C<) group-containing ligand, as the product.

The imine is reacted with the stoichiometric amount of a Group II metal β-diketonate complex of general formula [M(β-diketonate)$_2$]$_n$ (n=1–4) in an organic solvent to form a reaction product including a Group II metal β-diketonate complex including at least one imine (—N=C<)group-containing ligand dissolved in that solvent.

The solvent is removed, to recover the Group II metal β-diketonate complex including the imine (—N=C<) group-containing ligand, as the preferred product source reagent.

In another method (Synthesis 4) a polyamine with terminal —NH$_2$ groups is reacted with a stoichiometric amount of a carbonyl group-containing reagent in an organic solvent, in the presence or absence of a desiccant, to form a reaction product including at least one imine (—N=C<) group dissolved in the solvent.

Upon separation of the desiccant, if present, the solvent is removed from the reaction product, to give the imine (—N=C<) group-containing ligand, as the product.

The imine is reacted with the stoichiometric amount of a Group II metal β-diketonate complex of general formula [M(β-diketonate)$_2$]$_n$ (n=1–4) in an organic solvent to form a reaction product including a Group II metal β-diketonate complex including at least one imine (—N=C<) group-containing ligand dissolved in that solvent.

The solvent is removed, to recover the Group II metal β-diketonate complex including the imine (—N=C<) group-containing ligand, as the product source reagent.

In the above examples, the iminc is substituted with hydrogen, at least one alkyl group, or preferably with two alkyl groups that may be the same or different. The alkyl groups, if present, may be $C_1$–$C_{12}$ alkyl, perfluoroalkyl, or cycloalkyl species.

In the foregoing synthetic methods, the solvents used in the synthesis may be of any suitable type, including solvents such as alkanes, alkanols, aliphatic and cyclic ethers (e.g., alkane ethers), as well as any carbonyl species used in the reaction, if such carbonyl species is solubilizingly effective for the other reactant(s) in the reaction.

The dessicant optionally used in various of the foregoing synthetic methods may comprise any suitable species, such as for example $K_2CO_3$, that is compatible with the reactants and reaction products in the reaction in which the dessicant is used, and that is dessicatingly effective therein.

The source precursor formed in accordance with the above-described synthesis methods may be used to form a Group II metal-containing film on a substrate by volatilizing the reagent complex in liquid form, either as a neat liquid, or in a solution or suspension of the reagent complex in a suitable solvent. Such precursor liquid may for example be vaporized in a vaporizer of a liquid delivery apparatus such as a Sparta® vaporizer unit, commercially available from Advanced Technology Materials, Inc. (Danbury, Conn.), to form a corresponding precursor vapor. Other vaporizer designs including an aerosol, acoustic transducer or nebulizer may be used with equal success.

The precursor vapor then is transported to a chemical vapor deposition zone in which a wafer is provided on a heated susceptor. Upon contacting of the precursor vapor with the wafer, the metal component of the vapor is deposited on the wafer surface. The vapor may be delivered in the chemical vapor deposition chamber by a disperser such as a showerhead or nozzle, to provide a uniform flux of the vapor across the width of the wafer, to yield a correspondingly uniform thickness of deposited metal-containing film on the wafer. The process conditions (temperature, pressure, flow rate and composition of the vapor) may be suitably controlled to ensure an optimum process result for the MOCVD operation being conducted in the process system.

The Group II metal β-diketonate complex used in such MOCVD process may utilize an adduct of the present invention, incorporating ligands such as:

(i) aliphatic amines bearing terminal NH$_2$ groups;
(ii) aliphatic imines produced as the reaction product of an aliphatic amine ligand moiety (e.g., as specified in (i), an aliphatic amine bearing terminal NH$_2$ groups) and a carbonyl compound (e.g., containing at least one carbonyl group, such as a ketone, aldehyde, diketone or dialdehyde compound);
(iii) combination of two or more of the foregoing ligands (i)–(ii),
(iv) combination of at least one of the foregoing ligands (i)–(ii) with one or more other ligands or solvents, such as THF.

In one preferred application of the Group II source reagent complexes of the invention, a BST film is formed on a substrate, by providing liquid precursors for each of the barium, strontium and titanium components of the BST film, vaporizing each of the liquid precursors to form corresponding precursor vapor, and contacting the precursor vapor with a substrate to deposit barium, strontium and titanium thereon. In this method, at least one of the barium and strontium source reagent complexes is a β-diketonate adduct complex of the invention, and the precursor for the titanium component of the BST film preferably is $Ti(O\text{-}iPr)_2(thd)_2$ or other suitable Ti source.

The features and advantages of the invention, including specific adduct species of the invention, are more fully shown by the following non-limiting examples.

EXAMPLE 1

Synthesis and Characterization of the Material $Ba(thd)_2L_2$ Where L is Formed in the Condensation of Diethylenetriamine and Acetone a) Reaction of $Ba(thd)_2(deta)_2$ with Acetone A sample of $Ba(thd)_2(deta)_2$ was dissolved in acetone serving as a reagent and a solvent and stirred at room temperature for 16 hours. The excess acetone was removed under reduced pressure at room temperature and then followed by mild heating at 50–60° C. The resulting material had an appearance of a clear to slightly yellow viscous oil at room temperature. Its solubility in pentane was excellent. The material was characterized by several analytical and spectroscopic methods.

1) The elemental analysis was in good agreement with the theoretical formula, $Ba(thd)_2L_2$, where L is the imine ligand ($L^1$, $L^2$) shown below:

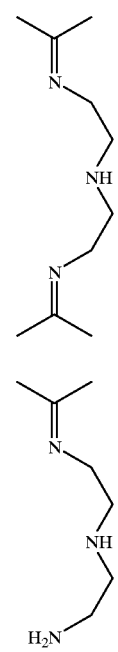

The corresponding elemental content (in %) is as follows:
theoretical, Ba, 15.77, C, 57.95, H, 9.26, N, 9.66,
experimental, Ba, 16.75, C, 57.64, H, 9.07, N, 9.18.

Figure 1B:
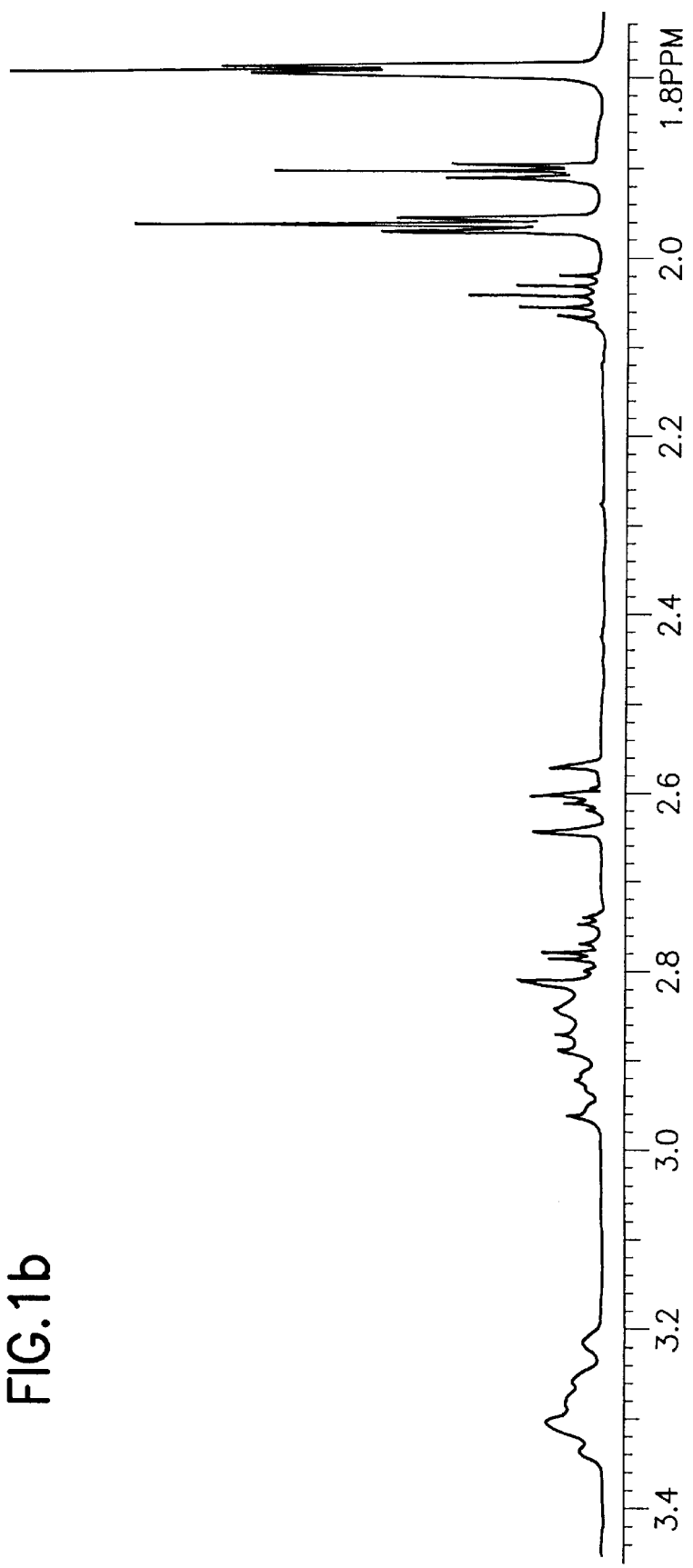

2) The $^1$H NMR spectrum (FIGS. 1a and 1b) collected from a sample dissolved in acetone-$d_6$ displayed a single magnetic environment for the thd ligands, the resonances for the deta ligands, which were different from those in the spectrum of $Ba(thd)_2(deta)_2$ and the presence of new and distinct resonances due to the methyl groups from reacted acetone appearing as triplets in the region of the spectrum between 2.00 and 1.75 ppm. These triplets with coupling constants of 1.5 and 0.7 Hz result from couplings of the imine methyl groups with the methylene groups adjacent to the terminal nitrogen atoms across the imine moiety in a trans and cis configuration, respectively:

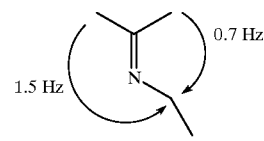

A separate set of NMR experiments allowed the monitoring of the condensation reaction and the confirmation of resonance assignments. The reaction with deuterated acetone yielded a product, which did not display the aforementioned triplets, thereby confirming that they represent the methyl groups of reacted acetone. The reaction with acetone in deuterated methanol showed that the reaction occured in this solvent at a faster rate and that the final product was the same as in the case when acetone is used both as a reagent and as a solvent.

Figure 2:
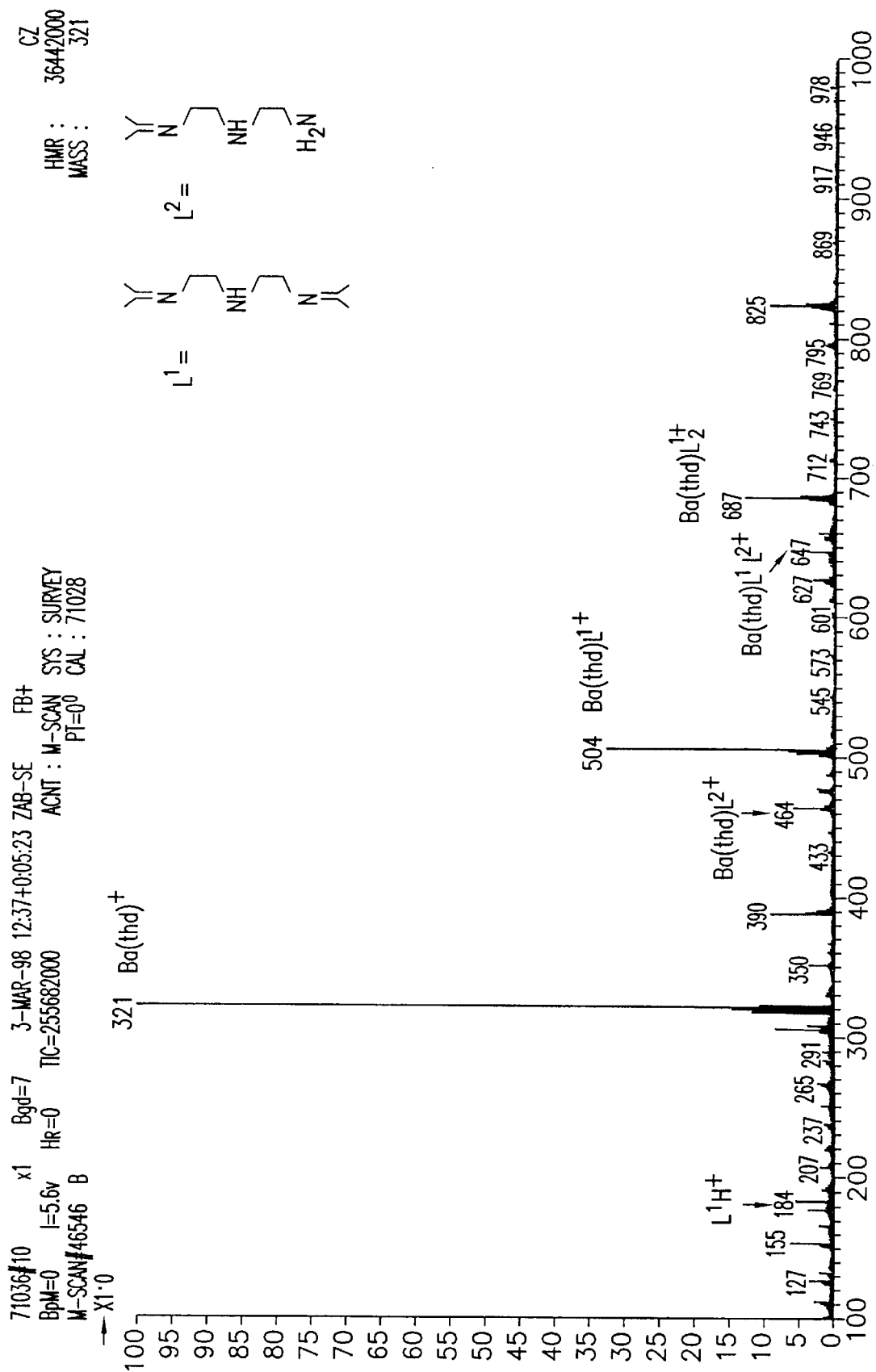
FIG. 2 is the mass spectrum of the product of reaction of Ba(thd)$_2$(deta)$_2$ with acetone.

3) The IR spectrum of the material (FIG. 2) displays a strong peak at 1665 $cm^{-1}$ which was not observed in the spectrum of $Ba(thd)_2(deta)_2$. This signal is assigned to the stretching mode $v(C=N)$. Such a signal is typically present at 1620–1680 $cm^{-1}$ in the IR spectra of imines. A second interesting feature is the absence of usually easily detectable water (3500 $cm^{-1}$, broad) in the spectrum of this material. The peaks at 3200–3400 $cm^{-1}$ are assigned to $v(N\text{---}H)$. These peaks are less intense and less complex in the spectrum of the oil compared to those in the spectrum of $Ba(thd)_2(deta)_2$.

4) The analysis for water content of one sample obtained from the reaction, where $K_2CO_3$ was used as a desiccant, displayed 0.15% of water. This result indicated that the water produced during the condensation reaction (7%) can be removed efficiently, but it also suggested that more complete desiccation may be desirable.

Figure 3:
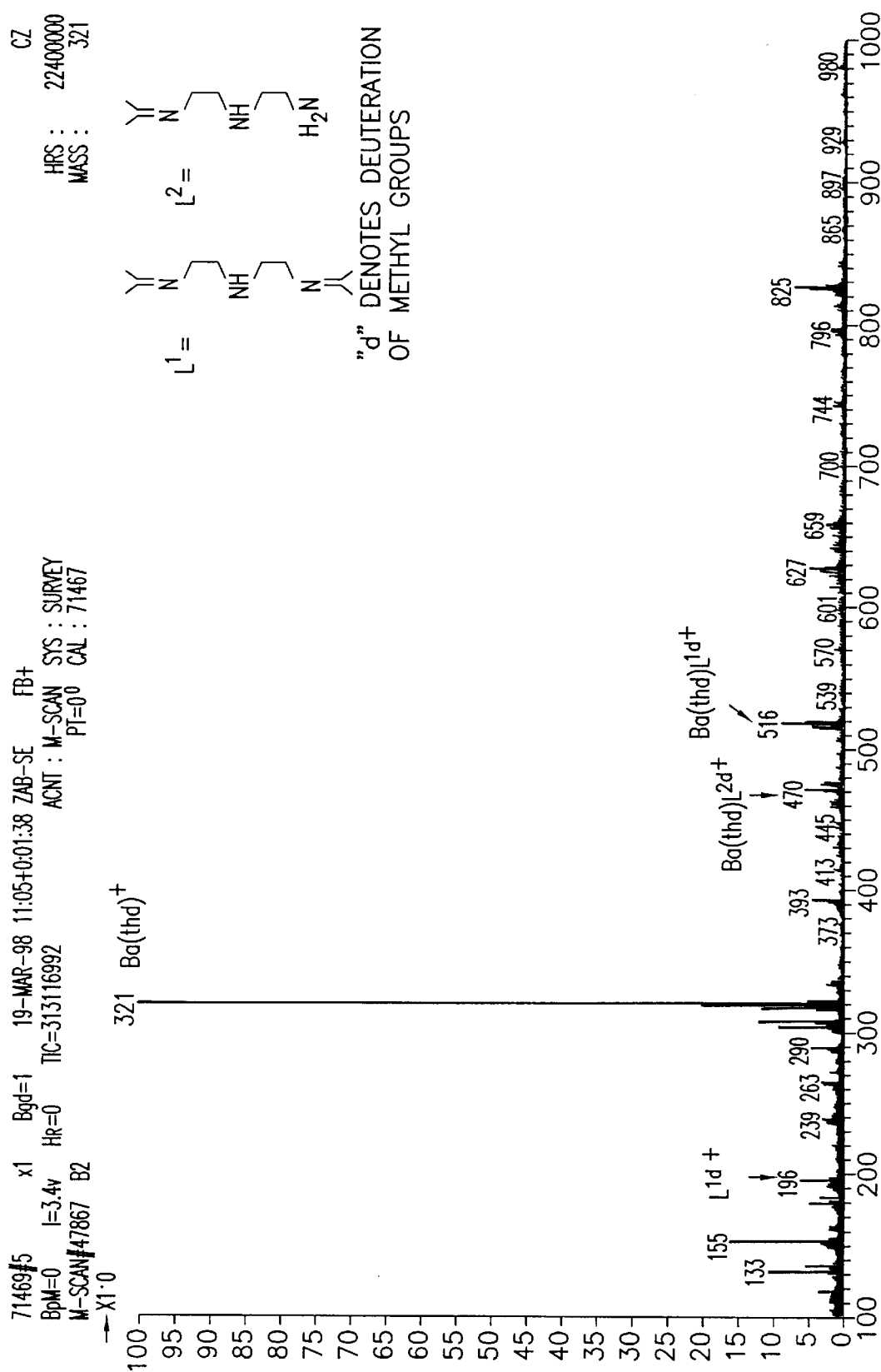
FIG. 3 is the mass spectrum of the product of reaction of Ba(thd)$_2$(deta)$_2$ with deuterated acetone.
Figure 4:
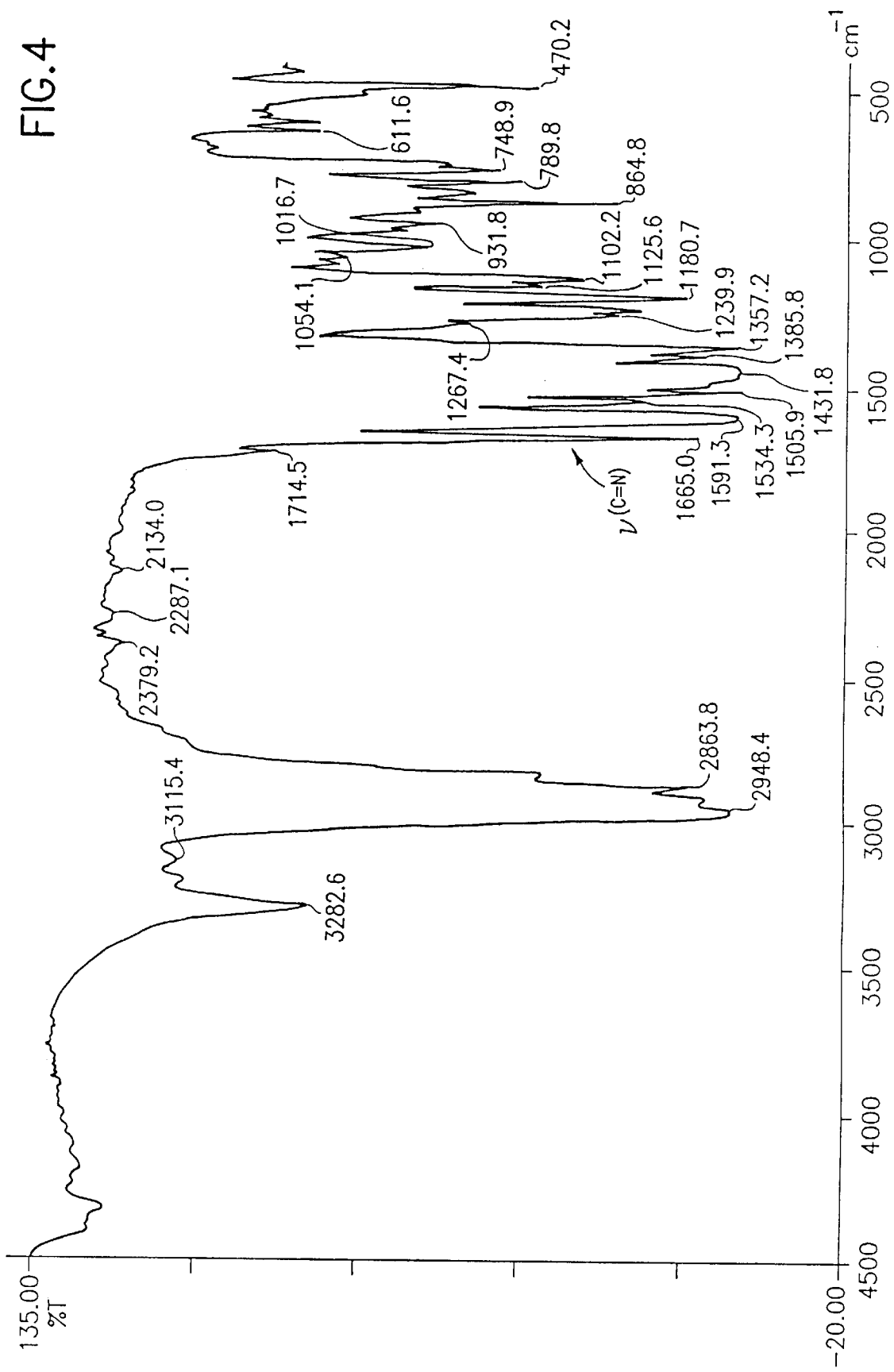
FIG. 4 is the infrared spectrum of the product of reaction of Ba(thd)$_2$(deta)$_2$ with acetone.

5) The analysis of the material by fast atom bombardment mass spectroscopy (FAB-MS) provided more structural information. The mass spectra carried out on regular (FIG. 3) as well as partially deuterated (FIG. 4) samples revealed that the material contains predominantly $Ba(thd)_2L_2^1$ but also $Ba(thd)_2L^1L^2$, where $L^1$ and $L^2$ are shown below:

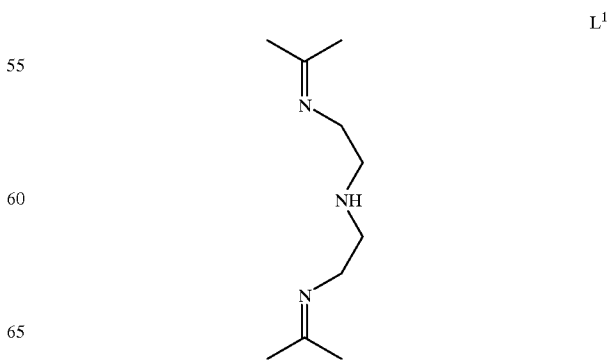

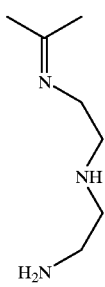

L²

Figure 5:
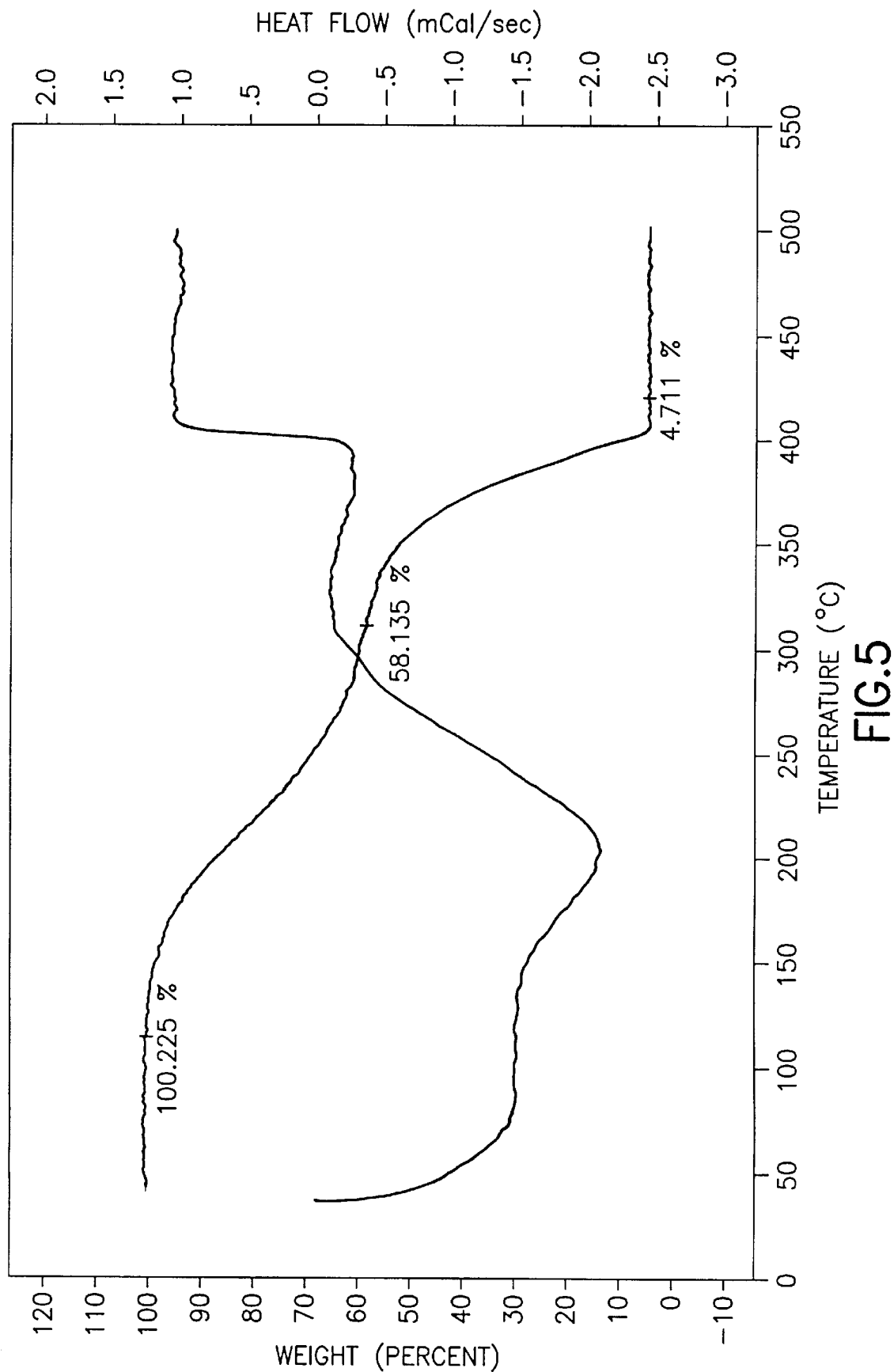
FIG. 5 shows the STA plots of the product of reaction of Ba(thd)$_2$(deta)$_2$ with acetone.

6) The simultaneous thermal analysis of the material (FIG. 5) displayed a low (5%) residual weight, reached at 410° C., indicating good volatility. The initial weight loss began at 150° C., but the loss was slower than that of the related complexes of the same general formula Ba(thd)$_2$L.

b) Reaction of [Ba(thd)$_2$]$_4$ with L Where L is Formed Independently From Deta and Acetone Diethylenetriamine was directly reacted with excess acetone in the presence of K$_2$CO$_3$ as desiccant. Upon separation of the desiccant and the removal of solvent the imine product was isolated. It was characterized by $^1$H NMR spectroscopy, which showed very similar resonances to those displayed by the material described in Example 1a, with the exception of thd resonances. The elemental analysis of the imine was consistent with the structure L$^1$:

theoretical, C, 65.5, H, 11.5, N, 22.9,
experimental, C, 64.8, H, 11.5, N, 23.3.

Figure 6:
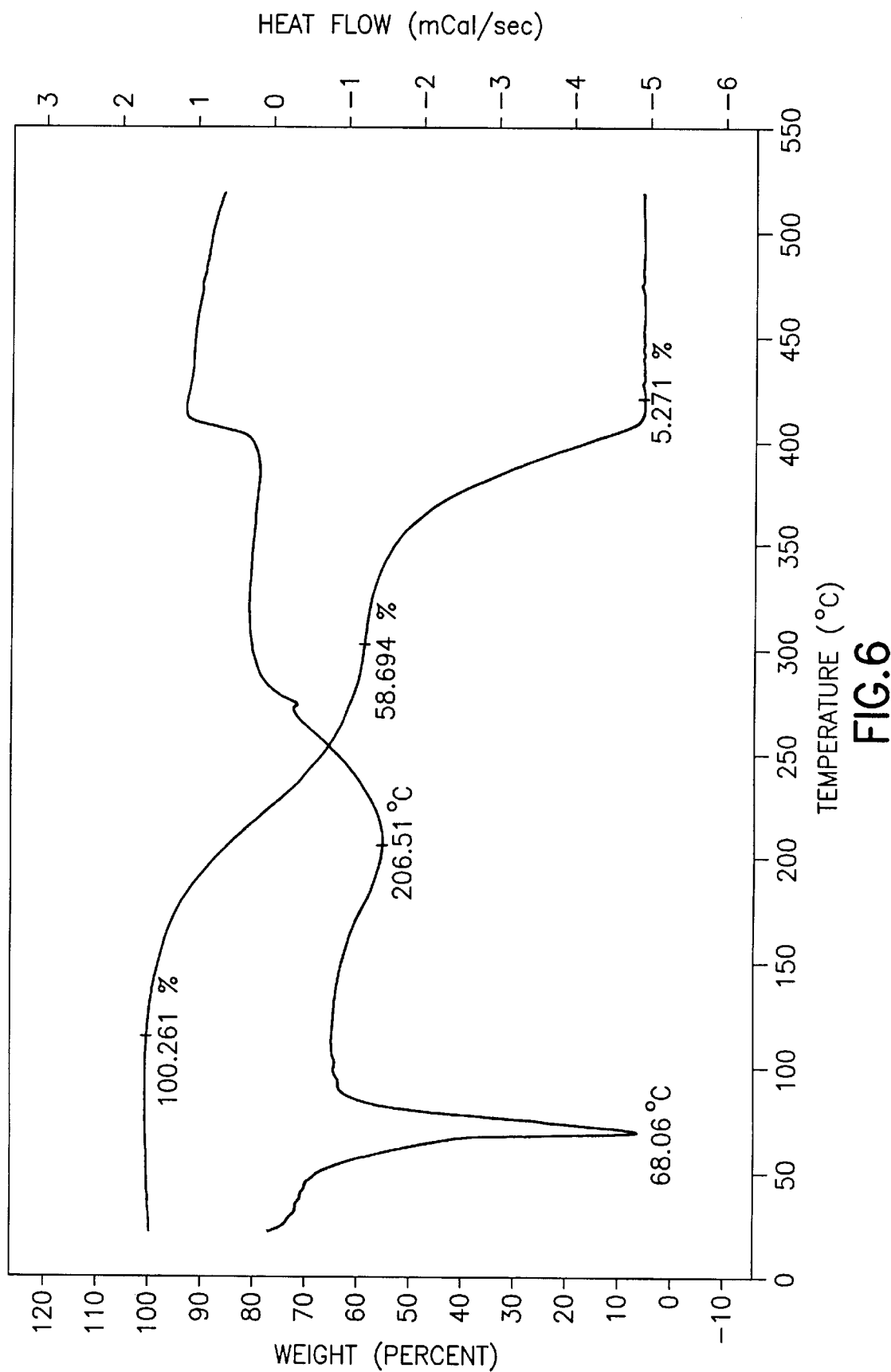
FIG. 6 shows the STA plots of Ba(thd)$_2$L$_2$, where L is the product of the reaction of deta with acetone.

This imine was used in a stoichiometric amount (2 equivalents) for the reaction with [Ba(thd)$_2$]$_4$ in pentane. After evaporation of the solvent, a solid material was obtained. The solid displayed virtually identical $^1$H NMR spectrum as the material described in Example 1a. It also displayed a very similar STA plots in argon (FIG. 6) with the exception of the strong melting endotherm in the DSC curve at 68° C. for this crystalline solid.

EXAMPLE 2

Synthesis and Characterization of the Material Sr(thd)$_2$L$_2$ From the Reaction of Sr(thd)$_2$(deta)$_2$ with Acetone A sample of Sr(thd)$_2$(deta)$_2$ was dissolved in acetone serving as a reagent and a solvent and stirred at room temperature for 16 hours. The excess acetone was removed under reduced pressure at room temperature, followed by mild heating to 50–60° C. The resulting material had an appearance of a clear to slightly yellow viscous oil at room temperature. Its solubility in pentane was excellent. The material was characterized by $^1$H NMR and STA (Ar).

The $^1$H NMR spectrum of the material was very similar to the Ba analog. Again, a single thd environment, changed deta resonances compared to those in Sr(thd)$_2$(deta)$_2$ and the presence of methyl triplets were observed.

Figure 7:
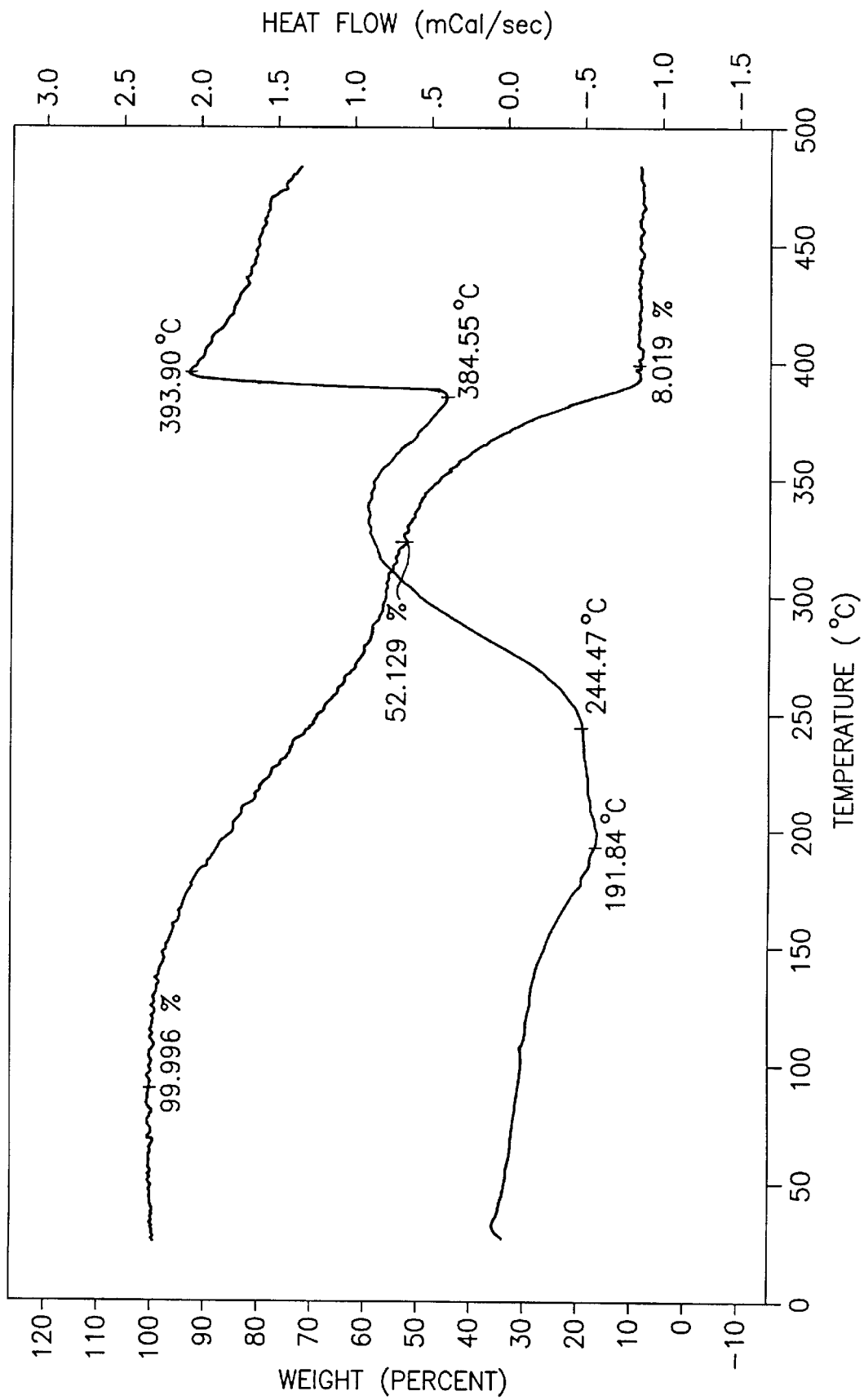
FIG. 7 shows the STA plots of the product of reaction of Sr(thd)$_2$(deta)$_2$ with acetone.

The STA analysis of the material in argon (FIG. 7) displayed a low (8%) residual weight, reached at 380° C., indicating good volatility. The initial weight loss began at 130° C. but the loss was slower than that of the related precursors of the same general formula Sr(thd)$_2$L.

EXAMPLE 3

Figure 8:
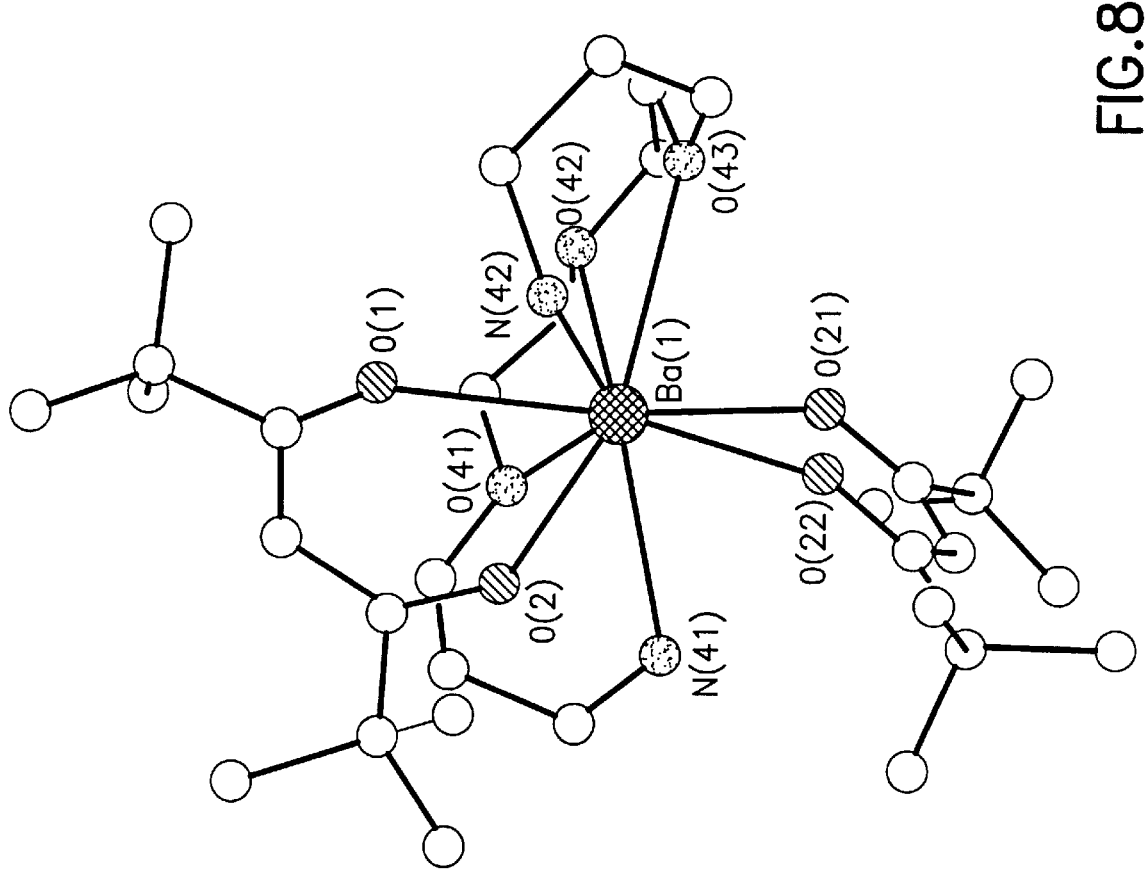
FIG. 8 shows the ORTEP diagram for Ba(thd)$_2$L, where L is 4,7,10-trioxa-1,13-tridecanediamine.

The Illustration of Metal Coordinated Polyamine→Imine Transformation in Ba(thd)$_2$L with 4,7,10-trioxa-1,13-tridecanediamine and the Corresponding Imine as L The solid state structure of Ba(thd)$_2$L, where L is 4,7,10-trioxa-1,13-tridecanediamine, was determined by X-ray crystallography and is shown in FIG. 8. It displays a typical geometry (observed previously for Ba(thd)$_2$(tetraglyme)) where the ligand L is positioned between the two β-diketonate ligands and occupies a pseudo equatorial plane around the metal center. All of the donor atoms (two N atoms and three O atoms) are coordinated to the Ba center. The average Ba—N distance is 2.96 Å. The structure indicates some steric congestion as one of the thd ligands is distorted.

The complex was reacted with acetone in the presence of K$_2$CO$_3$ as a desiccant. The product was isolated by separation of the desiccant, evaporation of acetone (which also served as a solvent) and recrystallization from cold pentane. The structure of the product was determined by X-ray crystallography (FIG. 9) and showed that the NH$_2$ groups in 4,7,10-trioxa-1,13-tridecanediamine had been transformed into imine moieties. The structure also showed that one of the imine nitrogen atoms is not coordinated to the Ba center, possibly due to the increased steric interactions associated with the transformation. The Ba—N (imine) distance is 2.91 Å and is shorter than in the Ba—N bond length in the analogous amine complex (FIG. 8). This suggests a stronger interaction between the Lewis base adduct ligand and the metal center and thus, greater stability of the complex.

The chemical transformation can be depicted by the drawing below:

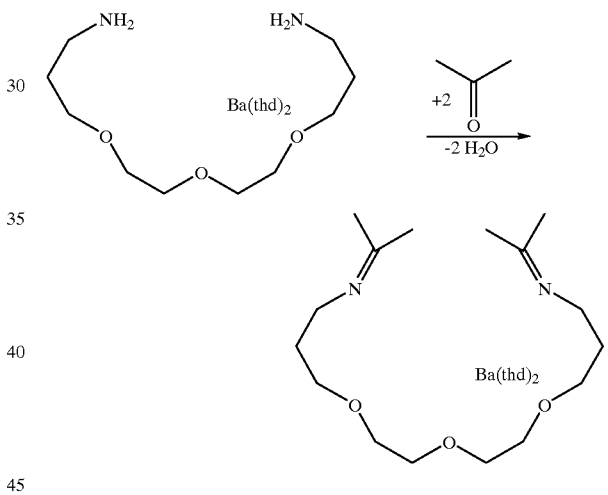

The spectroscopic characterization of the imine adduct displayed features, which are analogous to those described in Example 1. The $^1$H NMR spectrum displayed the presence of imine methyl triplets confirming their assignment. A strong ν(C=N) mode band was also observed in the IR spectrum of the complex after transformation.

EXAMPLE 4

Synthesis of Ba(thd)$_2$L Where L is an Imine Containing a Long Chain Alkyl Group The complex Ba(thd)$_2$L, where L is 4,7,10-trioxa-1,13-tridecanediamine, was reacted with a stoichiometric amount (two equivalents) of hexanal in methanol in the presence of K$_2$CO$_3$ as desiccant. The relatively high boiling point of 1-hexanal precluded its use as a solvent for this reaction. Upon separation of the desiccant, the methanol was evaporated and the material was isolated as light yellow oil. The $^1$H NMR spectrum displayed new resonances for the adduct ligand and a single thd environment. The imine H atoms were observed as triplet of triplets at 7.65 ppm resulting from couplings of 4.7 and 1.3 Hz to two different methylene groups: one attached to the same imine carbon atom and second attached to the imine nitrogen atom.

Figure 10:
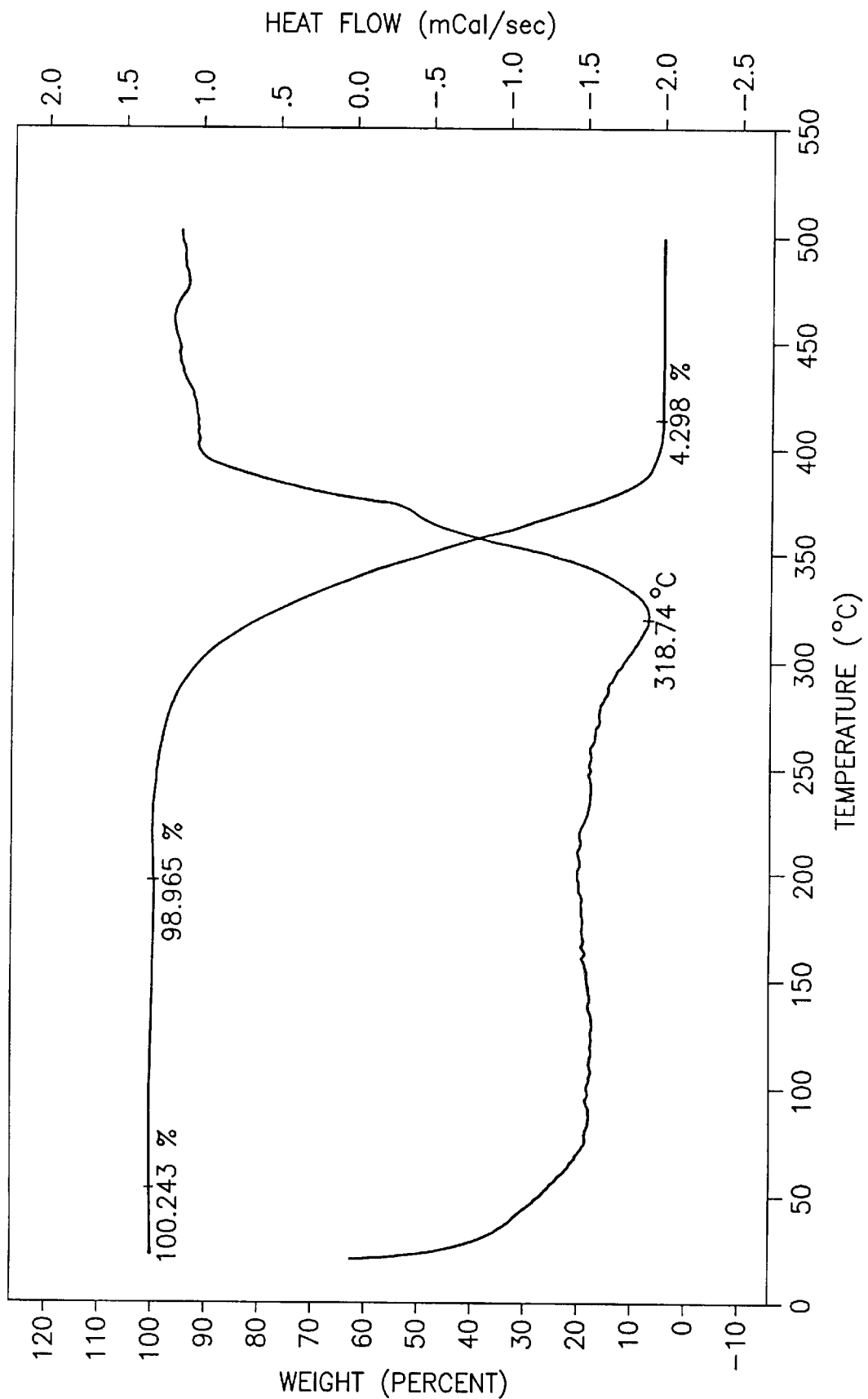
FIG. 10 shows the STA plots of Ba(thd)$_2$L, where L is the product of the reaction of 4,7,10-trioxa- 1,13-tridecanediamine with n-hexanal (n-pentylformaldehyde).

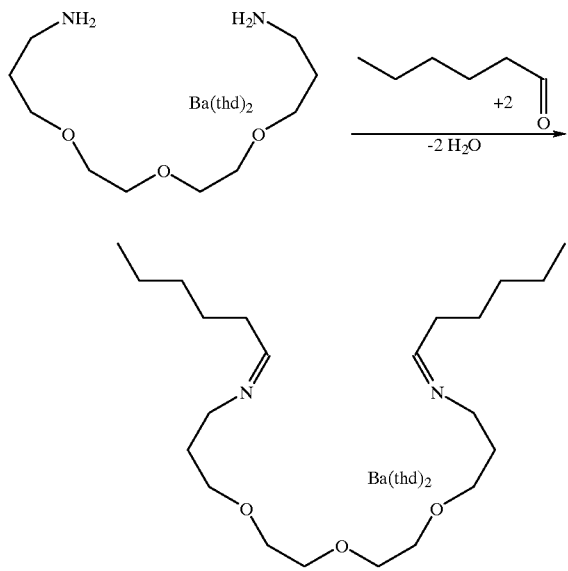

a) The STA analysis in argon (FIG. 10) revealed that the transport of the material occurred in one step beginning at ca. 270° C. and reached a low residual weight of 4% at 380° C. The latter temperature is lower relative to the values typical for Ba(thd)$_2$L complexes with different L ligands. The results are consistent with the beneficial character of the structure for the CVD process, with respect to the stability, volatility, and solubility of the precursor.

EXAMPLE 5

The Effect of Amine→Imine Condensation in Ba(thd)$_2$L on Physical State and Transport Properties of the Complexes Syntheses of several complexes of the general formula Ba(thd)$_2$L, where L is tetraglyme, a polyamine or the corresponding imine ligand with different alkyl groups attached to imine carbon atoms allowed the observation of the effect of structure-property relationships towards physical state and transport properties by examining:

(a) the amine→imine transformation and
(b) different groups attached to imine moieties of the Ba(thd)$_2$ compounds. These properties were analyzed by STA in argon and x-ray crystallography when possible. The data are presented in the table below and compared to the data obtained for the analogous tetraglyme and N,N,N',N'',N''-pentamethyldiethylenetriamine (pmdeta) complexes.

| ligand in Ba(thd)$_2$L | m.p.* [° C.] | temperature range of transport [° C.] | residual weight [%] |
| --- | --- | --- | --- |
| 2 imine with L$^1$ core, R$_1$ = R$_2$ = Me | 82 | 210–410 | 11 |
| 3 imine with L$^1$ core, R$_1$ = Me, R$_2$ = Et | 63 | 210–410 | −4** |
| 4 imine with L$^1$ core, R$_1$ = H, R$_2$ = n-pentyl | — | 270–380 | 5 |
| 5 L$^2$ = 1,5,8,12-tetraazadodecane | 141 | 200–420 | 10 |
| 6 imine with L$^2$ core, R$_1$ = R$_2$ = Me | 103 | 210–420 | 4 |
| 7 L$^3$ = 2,2'-(ethylenedioxy)bis(ethylamine) | 88 | 110–170 (2%) 190–420 | 7 |
| 8 imine with L$^3$ core, R$_1$ = R$_2$ = Me | 113 | 50–70 (2%) 180–410 | 5 |
| 9 imine with L$^3$ core, R$_1$ = Me, R$_2$ = n-hexyl | — | 230–370 | 4 |
| 10 tetraglyme | 105 | 160–410 | 4 |
| 11 N,N,N',N'',N''-pentamethyldiethylenetriamine (pmdeta) | 157 | 140–410 | 6 |

*strong endotherm in the STA
**instrumental error

Figure 11:
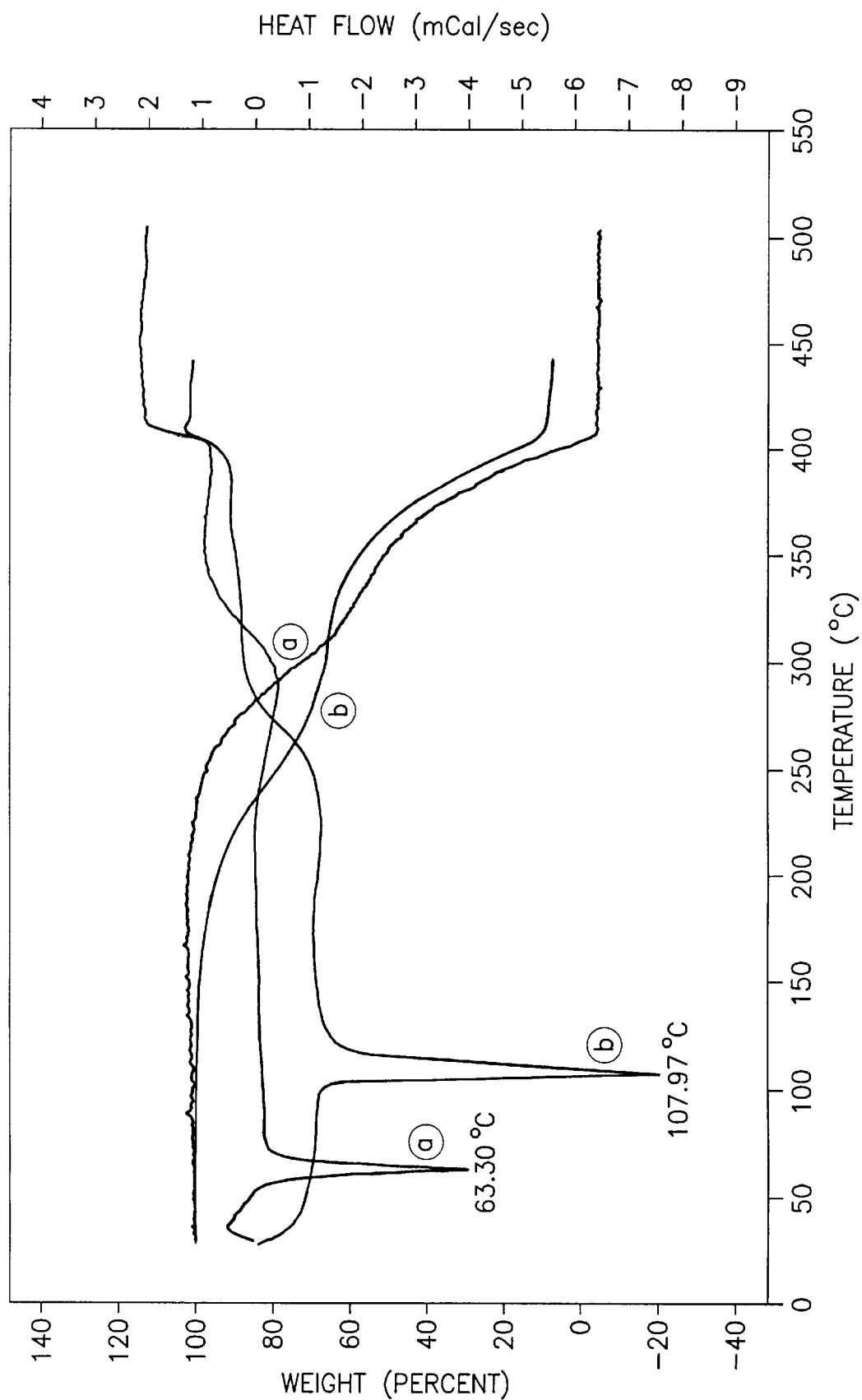
FIG. 11 compares the STA plots of Ba(thd)$_2$L complexes, where L is the product of the reaction of 4,7,10-trioxa-1,13-tridecanediamine with (a) 2-butanone and (b) where L is the product of the reaction of 4,7,10-trioxa- 1,13-tridecanediamine with tetraglyme.

These synthetic experimental studies allow several conclusions to be drawn:

1) All complexes in this group displayed useful volatilities.
2) The complexes with imine ligands began to transport at relatively higher temperature compared to the amine analogs and did not display ligand dissociation in a similar manner to the tetraglyme and pmdeta complexes under identical conditions.
3) The initial weight loss, which was assigned to the dissociation of the ligand L, was significantly slower for the imine and also higher polyamine ligands than for tetraglyme and pmdeta complexes (FIG. 11).
4) The introduction of longer chain alkyl groups to the imine moiety decreased the upper temperature limit for transport and resulted in a liquid physical state for the corresponding metal precursor.
5) The melting point of the complex can be lowered by introducing a long chain alkyl group and asymmetry to the imine moiety.

These results indicate that the condensation reactions allow one to modify the properties of the molecules. These modifications are beneficial for the production of low melting or liquid Group II precursors and provide utility for the CVD process.

While the invention has been illustratively described herein with reference to particular features, aspects and embodiments, it will be appreciated that the invention is not thus limited. The invention may be constituted and applied in other variations, modifications and other embodiments, as will readily suggest themselves to those of ordinary skill in the art, based on the disclosure herein. Accordingly, the claims hereafter set forth are to be correspondingly interpreted and construed, as encompassing within their spirit and scope all such variations, modifications and other embodiments.

Figure 9:
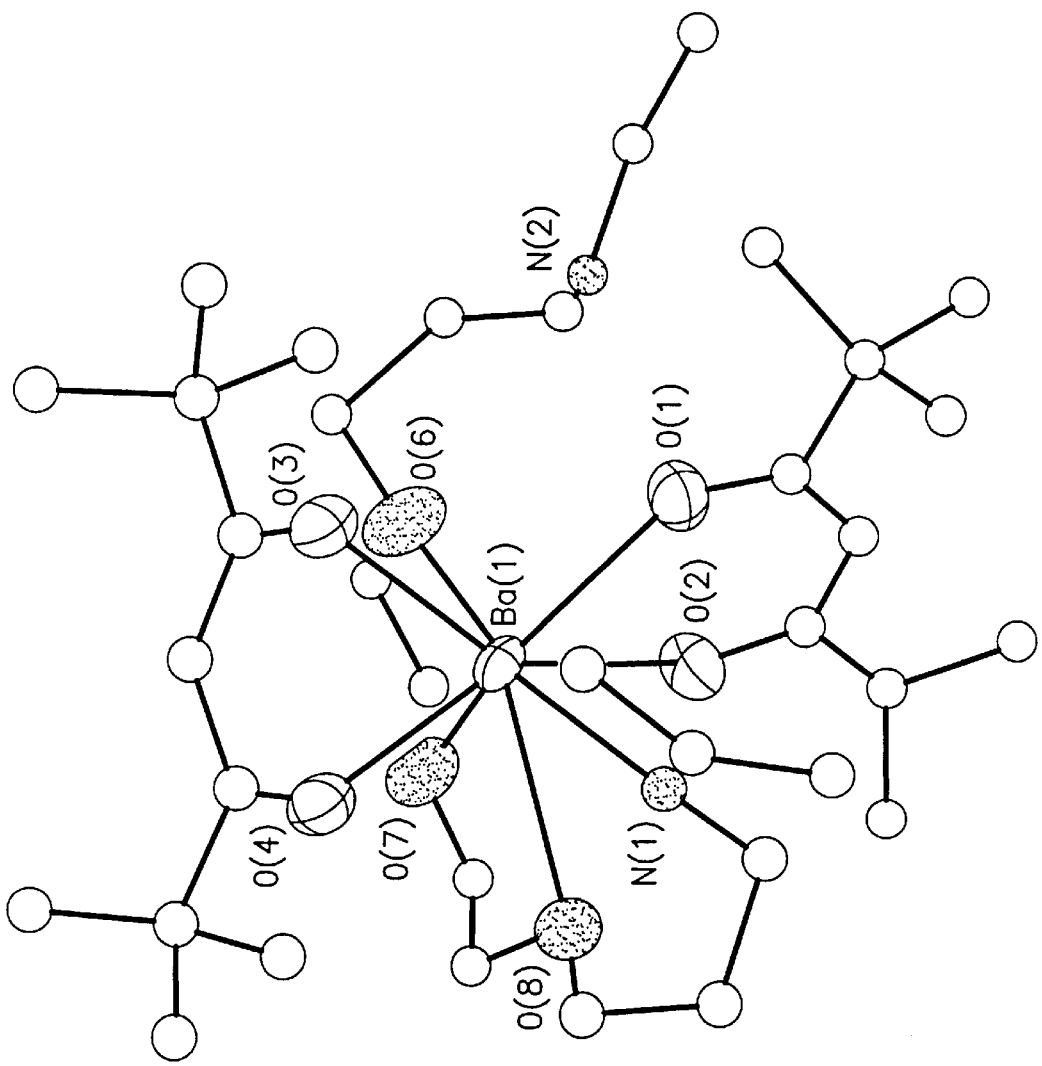
FIG. 9 shows the ORTEP diagram for Ba(thd)$_2$L, where L is the product of the reaction of 4,7,10-trioxa- 1,13-tridecanediamine with acetone.

What is claimed is:

1. A method for forming a Group II metal-containing film on a substrate, comprising the steps of:

providing a liquid delivery apparatus including a vaporizer and a chemical vapor deposition zone; transporting a liquid precursor composition for said Group II metal-containing film to the vaporizer of the liquid delivery apparatus for vaporization of the precursor composition to yield a vapor-phase Group II metal precursor composition; and flowing the vapor-phase Group II metal precursor composition to the chemical vapor deposition zone for subsequent deposition of the Group II metal-containing film on the substrate therein, using a liquid precursor material that includes barium bis(2,2,6,6-tetramethyl-3,5-heptanedionate) imine adduct having a generally clear viscous oil form, and the Ortep diagram structure illustrated in FIG. 8 or 9 hereof.

2. A method according to claim 1, wherein the Group II metal-containing film comprises BST.

3. A method according to claim 2, further comprising using a liquid precursor for the titanium component of the BST film, wherein said liquid precursor comprises Ti(O-iPr)$_2$(thd)$_2$.

4. A method according to claim 2, using a strontium bis(2,2,6,6-tetramethyl-3,5-heptanedionate) imine adduct having a clear or slightly yellow viscous oil form at 25° C., as a liquid precursor for the strontium component of tile BST film.

5. A liquid delivery process for forming a BST film on a substrate, comprising the steps of:

providing liquid precursors for each of the barium, strontium and titanium components of the BST film;

vaporizing each of the liquid precursors, separately or all together, to form the corresponding precursor vapor; and contacting the precursor vapor with a substrate to deposit barium, strontium and titanium thereon;

wherein said liquid precursors for barium includes bis(2,2,6,6tetramethyl-3,5-heptanedionate) imine adduct having a generally clear viscous oil form, and the Ortep diagram structure illustrated in FIG. 8 or 9 hereof.

6. A process according to claim 5, wherein the liquid precursor for the strontium component of the BST film comprises a strontium bis(2,2,6,6-tetramethyl-3,5-heptanedionate) imine adduct having a clear or slightly yellow viscous oil form at 25° C.

7. A process according to claim 5, wherein the liquid precursor for the strontium component of the BST film comprises a strontium bis(2,2,6,6-tetramethyl-3,5-heptanedionate) imine adduct having a clear or slightly yellow viscous oil form at 25° C.

8. A method for forming a Group II metal-containing film on a substrate, comprising the steps of:

providing a liquid delivery apparatus including a vaporizer and a chemical vapor deposition zone;

transporting a liquid precursor composition for said Group II metal-containing film to the vaporizer of the liquid delivery apparatus for vaporization of the precursor composition to yield a vapor-phase Group II metal precursor composition; and flowing the vapor-phase Group II metal precursor composition to the chemical vapor deposition zone for subsequent deposition of the Group II metal-containing film on the substrate therein, using a liquid precursor material that includes a Group II metal β-diketonate complex incorporating therein at least one adduct ligand selected from the group consisting of:

(i) imines having a formula $R_1R_2C=N-G-N=CR_1R_2$ wherein $R_1$ and $R_2$ are independently alkyl, fluoroalkyl or $R_1$ and $R_2$ together with the adjacent carbon atom form a cycloalkyl group, and wherein G is a divalent moiety selected from the group consisting of $(-CH_2-)_x$, $(-CH-)_x$, amine groups, ether groups, and combinations thereof, wherein x is from 1 to 10 inclusive; and (ii) imines having a formula $R_1R_2C=N-G-NH_2$ wherein $R_1$ and $R_2$ are independently alkyl, fluoroalkyl or $R_1$ and $R_2$ together with the adjacent carbon atom form a cycloalkyl group, and wherein G is as described in (i) above;

(iii) an amine having a formula $H_2N-G-NH_2$, wherein G is as described in (i) above;

(iv) other ligands or solvents;

with the proviso that at least one of said adduct ligands is selected from the group consisting of ligands of (i) and (ii).

9. A method according to claim 5, further comprising using a liquid precursor for the titaniuin component of the BST film, wherein said liquid precursor comprises Ti(O-iPr)$_2$(thd)$_2$.

* * * * *

UNITED STATES PATENT AND TRADEMARK OFFICE
CERTIFICATE OF CORRECTION

PATENT NO. : 6,338,873 B1
DATED : January 15, 2002
INVENTOR(S) : Witold Paw et al.

It is certified that error appears in the above-identified patent and that said Letters Patent is hereby corrected as shown below:

Column 9,
Line 52, delete "hfac=hexafluoroacctylacetonate" and substitute
-- hfac=hexafluoroacetylacetonate --.

Column 10,
Lines 66 and 67, delete "$(-CH_213)_x$, $(-CH-)_x$, and substitute -- $(CH_{2-})_x$, $(-CH-)_x$, --.

Column 11,
Line 51, delete "diethyienetriamine" and substitute -- diethylenetriamine --.

Signed and Sealed this

Fourteenth Day of January, 2003

JAMES E. ROGAN
*Director of the United States Patent and Trademark Office*